US011540933B2

(12) United States Patent
Honeyfield et al.

(10) Patent No.: US 11,540,933 B2
(45) Date of Patent: Jan. 3, 2023

(54) IMPLANTABLE MEDICAL DEVICE CONSTRAINT AND DEPLOYMENT APPARATUS

(71) Applicant: W. L. Gore & Associates, Inc., Newark, DE (US)

(72) Inventors: Evan Honeyfield, Flagstaff, AZ (US); Craig W. Irwin, Parks, AZ (US); Jacob B. Munger, Flagstaff, AZ (US); Tyson J. Skelton, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/755,743

(22) PCT Filed: Oct. 10, 2018

(86) PCT No.: PCT/US2018/055223

§ 371 (c)(1),
(2) Date: Apr. 13, 2020

(87) PCT Pub. No.: WO2019/075069

PCT Pub. Date: Apr. 18, 2019

(65) Prior Publication Data

US 2020/0323670 A1 Oct. 15, 2020

Related U.S. Application Data

(60) Provisional application No. 62/570,732, filed on Oct. 11, 2017.

(51) Int. Cl.
*A61F 2/966* (2013.01)

(52) U.S. Cl.
CPC ............ *A61F 2/966* (2013.01); *A61F 2/9661* (2020.05); *A61F 2250/001* (2013.01); *A61F 2250/0039* (2013.01)

(58) Field of Classification Search
CPC ........ A61F 2/966; A61F 2/962; A61F 2/9661; A61F 2/9662; A61F 2/97; A61F 2/95;
(Continued)

(56) References Cited

U.S. PATENT DOCUMENTS 4,553,545 A 11/1985 Maass et al.
4,732,152 A 3/1988 Wallsten et al.
(Continued)

FOREIGN PATENT DOCUMENTS

CN 102341145 A 2/2012
CN 104023677 A 9/2014
(Continued)

OTHER PUBLICATIONS

International Search Report and Written Opinion from PCT/US2018/055223, dated Feb. 11, 2019, 14 pages.
(Continued)

*Primary Examiner* — Diane D Yabut

(57) ABSTRACT

An implantable device delivery system is disclosed. The delivery system includes a constraining member situated between an interior layer and an exterior layer of a cover. The interior layer of the cover is disposed about an implantable medical device, and the exterior layer of the cover extends over a portion of the interior layer. The cover is generally tapered to minimize deployment forces. The constraining member is disposed about a portion of the interior layer and operates to constrain the implantable device to a delivery configuration. The cover and the constraining member are generally configured to be removed concurrently during deployment of the implantable device.

21 Claims, 10 Drawing Sheets

(58) Field of Classification Search
CPC ............ A61F 2/9525; A61F 2002/9623; A61F 2002/9665
See application file for complete search history.

(56) References Cited

U.S. PATENT DOCUMENTS 4,848,343 A 7/1989 Wallsten et al.
4,921,479 A 5/1990 Grayzel
5,064,435 A 11/1991 Porter
5,389,100 A 2/1995 Bacich et al.
5,425,765 A 6/1995 Tiefenbrun et al.
5,445,646 A 8/1995 Euteneuer et al.
5,571,135 A 11/1996 Fraser et al.
5,647,857 A 7/1997 Anderson et al.
5,662,703 A 9/1997 Yurek
5,755,769 A 5/1998 Richard et al.
5,824,041 A 10/1998 Lenker et al.
5,989,280 A 11/1999 Euteneuer et al.
6,004,328 A 12/1999 Solar
6,019,787 A 2/2000 Richard et al.
6,039,721 A 3/2000 Johnson et al.
6,042,605 A 3/2000 Martin et al.
6,059,813 A 5/2000 Vrba et al.
6,113,608 A 9/2000 Monroe et al.
6,203,550 B1 3/2001 Olson
6,224,627 B1 5/2001 Armstrong et al.
6,238,410 B1 5/2001 Vrba et al.
6,254,628 B1 7/2001 Wallace et al.
6,315,792 B1 11/2001 Armstrong et al.
6,334,867 B1 1/2002 Anson
6,350,278 B1 2/2002 Lenker et al.
6,352,553 B1 3/2002 Van et al.
6,352,561 B1 3/2002 Leopold et al.
6,364,904 B1 4/2002 Smith
6,383,171 B1 5/2002 Gifford et al.
6,398,758 B1 6/2002 Jacobsen et al.
6,524,335 B1 2/2003 Hartley et al.
6,533,806 B1 3/2003 Sullivan et al.
6,544,278 B1 4/2003 Vrba et al.
6,607,552 B1 8/2003 Hanson
6,645,242 B1 11/2003 Quinn
6,676,693 B1 1/2004 Belding et al.
6,733,521 B2 5/2004 Chobotov et al.
6,790,225 B1 9/2004 Shannon et al.
6,899,728 B1 5/2005 Phillips et al.
6,911,039 B2 6/2005 Shiu et al.
6,942,682 B2 9/2005 Vrba et al.
6,949,112 B1 9/2005 Sridharan et al.
6,974,471 B2 12/2005 Van et al.
7,081,132 B2 7/2006 Cook et al.
7,147,661 B2 12/2006 Chobotov et al.
7,198,636 B2 4/2007 Cully et al.
7,201,770 B2 4/2007 Johnson et al.
7,285,130 B2 10/2007 Austin
7,425,219 B2 9/2008 Quadri
7,632,296 B2 12/2009 Malewicz
7,645,298 B2 1/2010 Hartley et al.
7,655,034 B2 2/2010 Mitchell et al.
7,753,945 B2 7/2010 Bruun et al.
7,794,488 B2 9/2010 Vrba et al.
7,828,837 B2 11/2010 Khoury
7,837,724 B2 11/2010 Keeble et al.
7,938,851 B2 5/2011 Olson et al.
7,955,370 B2 6/2011 Gunderson
7,976,575 B2 7/2011 Hartley
8,016,872 B2 9/2011 Parker
8,147,538 B2 4/2012 Brown et al.
8,167,926 B2 5/2012 Hartley et al.
8,167,927 B2 5/2012 Chobotov
8,231,665 B2 7/2012 Kim et al.
8,241,346 B2 8/2012 Chobotov
8,257,431 B2 9/2012 Henderson et al.
8,262,671 B2 9/2012 Osypka
8,317,854 B1 11/2012 Ryan et al.
8,328,861 B2 12/2012 Martin et al.
8,361,135 B2 1/2013 Dittman
8,435,282 B2 5/2013 Silverman
8,480,725 B2 7/2013 Rasmussen et al.
8,540,760 B2 9/2013 Paul et al.
8,641,752 B1 2/2014 Holm et al.
8,764,816 B2 7/2014 Koss et al.
8,801,774 B2 8/2014 Silverman
8,845,712 B2 9/2014 Irwin et al.
8,936,634 B2 1/2015 Irwin et al.
8,968,384 B2 3/2015 Pearson et al.
9,060,895 B2 6/2015 Hartley et al.
9,114,037 B2 8/2015 Silverman
9,132,025 B2 9/2015 Aristizabal et al.
9,186,487 B2 11/2015 Dubrul et al.
9,254,204 B2 2/2016 Roeder et al.
9,308,349 B2 4/2016 Rezac et al.
9,498,361 B2 11/2016 Roeder et al.
9,526,641 B2 12/2016 Irwin et al.
9,585,743 B2 3/2017 Cartledge et al.
9,585,774 B2 3/2017 Aristizabal et al.
9,668,853 B2 6/2017 Shin
9,681,968 B2 6/2017 Goetz et al.
9,700,701 B2 7/2017 Benjamin et al.
9,763,819 B1 9/2017 Sondreaal
9,782,284 B2 10/2017 Hartley et al.
9,907,641 B2 3/2018 Johnson
9,937,070 B2 4/2018 Skelton et al.
10,213,329 B2 2/2019 Cully et al.
10,405,966 B2 9/2019 Johnson
2001/0044595 A1 11/2001 Reydel et al.
2001/0056295 A1 12/2001 Solem
2002/0002397 A1 1/2002 Martin et al.
2002/0038141 A1 3/2002 Yang et al.
2002/0099431 A1 7/2002 Armstrong et al.
2002/0138129 A1 9/2002 Armstrong et al.
2003/0004561 A1 1/2003 Bigus et al.
2003/0105508 A1 6/2003 Johnson et al.
2003/0135258 A1 7/2003 Andreas et al.
2003/0176910 A1 9/2003 Vrba et al.
2003/0199966 A1 10/2003 Shiu et al.
2003/0199967 A1 10/2003 Hartley et al.
2003/0212410 A1 11/2003 Stenzel et al.
2004/0087886 A1 5/2004 Gellman
2004/0092977 A1 5/2004 Vargas et al.
2004/0143272 A1 7/2004 Cully et al.
2004/0143315 A1 7/2004 Bruun et al.
2004/0211433 A1 10/2004 Albright
2005/0049675 A1 3/2005 Wallace
2005/0059923 A1 3/2005 Gamboa
2005/0165352 A1 7/2005 Henry et al.
2005/0240254 A1 10/2005 Austin
2006/0015135 A1 1/2006 Vrba et al.
2006/0015171 A1 1/2006 Armstrong
2006/0030923 A1 2/2006 Gunderson
2006/0030924 A1 2/2006 Van et al.
2006/0041302 A1 2/2006 Malewicz
2006/0089627 A1 4/2006 Burnett et al.
2006/0122685 A1 6/2006 Bonsignore et al.
2006/0173422 A1 8/2006 Reydel et al.
2006/0184226 A1 8/2006 Austin
2006/0200221 A1 9/2006 Malewicz
2006/0206123 A1 9/2006 Brenneman
2007/0055358 A1 3/2007 Krolik et al.
2007/0060999 A1 3/2007 Randall et al.
2007/0093886 A1 4/2007 Cully et al.
2007/0142904 A1 6/2007 Sorenson et al.
2007/0191925 A1 8/2007 Dorn
2007/0208350 A1 9/2007 Gunderson
2007/0219612 A1 9/2007 Andreas et al.
2007/0244540 A1 10/2007 Pryor
2008/0140003 A1 6/2008 Bei et al.
2008/0140173 A1 6/2008 Eskaros et al.
2008/0167705 A1 7/2008 Agnew
2008/0255580 A1 10/2008 Hoffman et al.
2008/0281398 A1 11/2008 Koss et al.
2009/0018501 A1 1/2009 Yribarren et al.
2009/0099638 A1 4/2009 Grewe
2009/0125093 A1 5/2009 Hansen
2009/0143713 A1 6/2009 Van et al.

(56) References Cited

U.S. PATENT DOCUMENTS

2009/0182411 A1 7/2009 Irwin et al.
2009/0192584 A1 7/2009 Gerdts et al.
2009/0254063 A1 10/2009 Oepen et al.
2009/0270969 A1 10/2009 Fargahi et al.
2009/0299449 A1 12/2009 Styrc
2009/0326449 A1 12/2009 Wang et al.
2010/0004606 A1 1/2010 Hansen et al.
2010/0023106 A1 1/2010 Meyer et al.
2010/0036360 A1 2/2010 Herbowy et al.
2010/0036472 A1 2/2010 Papp
2010/0069852 A1 3/2010 Kelley
2010/0094398 A1 4/2010 Malewicz
2010/0100170 A1 4/2010 Tan et al.
2010/0168835 A1 7/2010 Dorn
2010/0234933 A1 9/2010 Punga et al.
2010/0331955 A1 12/2010 Vrba et al.
2011/0009943 A1 1/2011 Paul et al.
2011/0015716 A1 1/2011 Silverman
2011/0022154 A1 1/2011 Hamer et al.
2011/0034987 A1 2/2011 Kennedy
2011/0118765 A1 5/2011 Aguirre
2011/0118817 A1 5/2011 Gunderson et al.
2011/0137401 A1 6/2011 Dorn et al.
2011/0137402 A1 6/2011 Dorn et al.
2011/0166637 A1 7/2011 Irwin et al.
2011/0208292 A1 8/2011 Von et al.
2012/0016454 A1 1/2012 Jantzen et al.
2012/0059448 A1 3/2012 Parker et al.
2012/0078343 A1 3/2012 Fish
2012/0120287 A1 5/2012 Funamoto et al.
2012/0130472 A1 5/2012 Shaw
2012/0130473 A1 5/2012 Norris et al.
2012/0130474 A1 5/2012 Buckley
2012/0143306 A1 6/2012 Cully et al.
2012/0165915 A1 6/2012 Melsheimer et al.
2012/0193018 A1 8/2012 Banas et al.
2012/0239134 A1 9/2012 Dierking
2012/0296406 A1 11/2012 Minion
2012/0296412 A1 11/2012 Paul et al.
2012/0323315 A1 12/2012 Bruchman et al.
2013/0006220 A1 1/2013 Yribarren et al.
2013/0035749 A1 2/2013 Farag
2013/0150949 A1 6/2013 Silverman
2013/0158524 A1 6/2013 Fargahi
2013/0204343 A1 8/2013 Shalev
2013/0204345 A1 8/2013 Cully et al.
2013/0211493 A1 8/2013 Wubbeling et al.
2013/0238080 A1 9/2013 Silverman
2013/0245742 A1 9/2013 Norris
2013/0274851 A1 10/2013 Kelly
2013/0296877 A1 11/2013 Irwin et al.
2013/0340233 A1 12/2013 Tollner et al.
2014/0018610 A1 1/2014 Von Pechmann et al.
2014/0081376 A1 3/2014 Burkart et al.
2014/0130475 A1 5/2014 Van et al.
2014/0135895 A1 5/2014 Andress et al.
2014/0358156 A1 12/2014 Argentine
2015/0134043 A1 5/2015 Irwin et al.
2015/0196383 A1 7/2015 Johnson
2015/0250630 A1 9/2015 Irwin et al.
2016/0045349 A1 2/2016 Kilgrow et al.
2017/0172724 A1 6/2017 Cartledge et al.
2017/0281382 A1 10/2017 Lostetter et al.
2019/0247210 A1 8/2019 Cully et al.
2020/0022800 A1 1/2020 Johnson
2021/0186725 A1 6/2021 Irwin et al.

FOREIGN PATENT DOCUMENTS

CN 106102596 A 11/2016
DE 19531659 A1 3/1997
EP 1779809 A1 5/2007
EP 1441668 B1 1/2008
EP 1915113 B1 3/2010
EP 2175813 A1 4/2010
EP 2352464 A1 8/2011
EP 1358903 B1 11/2011
EP 2491894 A1 8/2012
EP 1474074 B1 4/2014
EP 2749251 B1 7/2016
EP 2956198 B1 11/2017
JP 2000-279532 A 10/2000
JP 2002-518086 A 6/2002
JP 2002-537026 A 11/2002
JP 2006-006648 A 1/2006
JP 2007-534441 A 11/2007
JP 2010-526583 A 8/2010
JP 2011-509744 A 3/2011
JP 2013-048778 A 3/2013
JP 2017-511725 A 4/2017
WO 98/08456 A1 3/1998
WO 98/26731 A2 6/1998
WO 99/65420 A1 12/1999
WO 00/48645 A2 8/2000
WO 01/01886 A1 1/2001
WO 01/22903 A2 4/2001
WO 02/38084 A2 5/2002
WO 2005/107644 A1 11/2005
WO 2008/034793 A1 3/2008
WO 2008/137177 A2 11/2008
WO 2009/012061 A1 1/2009
WO 2009/091603 A1 7/2009
WO 2009/145901 A1 12/2009
WO 2010/063794 A1 6/2010
WO 2010/063795 A1 6/2010
WO 2010/120671 A1 10/2010
WO 2011/076408 A1 6/2011
WO 2012/054178 A1 4/2012
WO 2013/025470 A2 2/2013

OTHER PUBLICATIONS

International Preliminary Reporton Patentability received for PCT Patent Application No. PCT/US2018/055223, dated Apr. 23, 2020, 9 pages.

IMPLANTABLE MEDICAL DEVICE CONSTRAINT AND DEPLOYMENT APPARATUS

CROSS-REFERENCE TO RELATED APPLICATION

This application is a national phase application of PCT Application No. PCT/US2018/055223, filed Oct. 10, 2018, which claims the benefit of U.S. Provisional Application No. 62/570,732, filed Oct. 11, 2017, both of which are incorporated herein by reference in their entireties for all purposes.

This listing of claims will replace all prior versions and listings of the claims in this application.

BACKGROUND

The present disclosure is related to devices and methods for delivering and deploying implantable medical devices.

A continued interest exists in developing improved devices and methods to effectively constrain, deliver, and/or deploy implantable medical devices (e.g., stents, stent-grafts, balloons, filters, occluders, and the like) through minimally invasive procedures.

In some instances, implantable devices and treatment apparatuses may be covered or coated with drugs or other bioactive agents. These devices present additional challenges for effective constraint, delivery, and deployment because risks exist that the coverings or coatings may be removed, damaged, or displaced during assembly and/or deployment, which could compromise the device's effectiveness once deployed.

SUMMARY

According to one example, ("Example 1"), a medical system includes an expandable endoprosthesis having a proximal end and a distal end, an elongate member having a proximal end and a distal end, the expandable endoprosthesis being situated along the elongate member proximate the distal end of the elongate member, a tubular cover having a first end and a second end, the cover including a first portion and a second portion, the first portion being disposed about the expandable endoprosthesis and the second portion extending over at least part of the first portion, the first portion having a diameter change such that a first end of the first portion has a smaller diameter than a second end of the first portion, and a constraining member disposed about the expandable endoprosthesis such that the constraining member is situated between the first and second portions of the tubular cover, the constraining member constraining the expandable endoprosthesis in a delivery configuration.

According to another example, ("Example 2"), further to Example 1, the second portion is everted over the first portion.

According to another example, ("Example 3"), further to any of Examples 1 to 2, the first portion of the tubular cover has a tapered profile.

According to another example, ("Example 4"), further to Example 3, the tapered profile of the first portion includes a plurality of discrete steps having differing diameters.

According to another example, ("Example 5"), further to any of the preceding Examples, the tubular cover has a progressive taper from the first end of the tubular cover to the second end of the tubular cover.

According to another example, ("Example 6"), further to any of the preceding Examples, the second portion includes a diameter change.

According to another example, ("Example 7"), further to Example 6, the tubular cover includes a plurality of stepped discrete cylindrical sections having different diameters.

According to another example, ("Example 8"), further to Example 7, for each stepped discrete cylindrical section, the stepped discrete cylindrical section has a length and wherein a diameter is substantially constant along the length.

According to another example, ("Example 9"), further to Example 7, one or more of the stepped discrete cylindrical sections is tapered.

According to another example, ("Example 10"), further to any of the preceding Examples, the first portion contacts the expandable endoprosthesis.

According to another example, ("Example 11"), further to any of the preceding Examples, the expandable endoprosthesis is self-expandable.

According to another example, ("Example 12"), further to Example 1, the second portion has a length and a substantially constant diameter along the length.

According to another example, ("Example 13"), further to Example 1, the second portion is tapered such that a proximal end of the second portion has a larger diameter than a distal end of the second portion.

According to another example, ("Example 14"), an implantable medical device deployment system includes an inner shaft having a distal end and proximal end, the medical device mounted on the inner shaft proximate the distal end of the inner shaft, and a sleeve that constrains the medical device prior to a deployment of the medical device, the sleeve adapted to unwrap from the medical device during deployment, the sleeve having a length, wherein the sleeve is partially everted over itself prior to the deployment of the medical device, and wherein the sleeve includes a first section and a second section, the second section having an increased diameter relative to the first section.

According to another example, ("Example 15"), further to Example 14, the sleeve includes a third section having an increased diameter relative to the second section.

According to another example, ("Example 16"), further to Example 15, the second section is positioned distal to the first section and wherein the third section is positioned distal to the second section.

According to another example, ("Example 17"), an implantable medical device deployment system includes an inner shaft having a distal end and proximal end, the medical device mounted on the inner shaft near the distal end, and a knitted constraining element having a first portion and a second portion, the first portion being disposed about the medical device prior to a deployment of the medical device such that the medical device has a constrained outer diameter, the knitted constraining element being configured such that it can be deconstructed during its removal from the medical device during the deployment of the medical device, wherein the second portion of the knitted constraining element extends distal to a distal end of the medical device, the second portion of the knitted constraining element being axially compressed such that it forms a scrunched portion.

According to another example, ("Example 18"), further to Example 17, the system further includes a proximal support element.

According to another example, ("Example 19"), further to Example 17, the system further includes a distal step element.

According to another example, ("Example 20"), a medical system includes an expandable endoprosthesis having a proximal end and a distal end, an elongate member having a proximal end and a distal end, the expandable endoprosthesis being situated along the elongate member proximate the distal end of the elongate member, and a tubular cover having a first end and a second end, the tubular cover including a first portion and a second portion, the first portion being disposed about the expandable endoprosthesis and the second portion extending over at least part of the first portion, wherein at least the first portion has a plurality of discrete steps along its length.

According to another example, ("Example 21"), further to Example 20, the system further includes a knitted constraining element situated between the first and second portions of the tubular cover.

While multiple embodiments are disclosed, still other embodiments will become apparent to those skilled in the art from the following detailed description, which shows and describes illustrative examples. Accordingly, the drawings and detailed description are to be regarded as illustrative in nature and not restrictive.

BRIEF DESCRIPTION OF THE DRAWINGS

The accompanying drawings are included to provide a further understanding of inventive embodiments of the disclosure and are incorporated in and constitute a part of this specification, illustrate examples, and together with the description serve to explain inventive principles of the disclosure.

DETAILED DESCRIPTION

Figure 1:
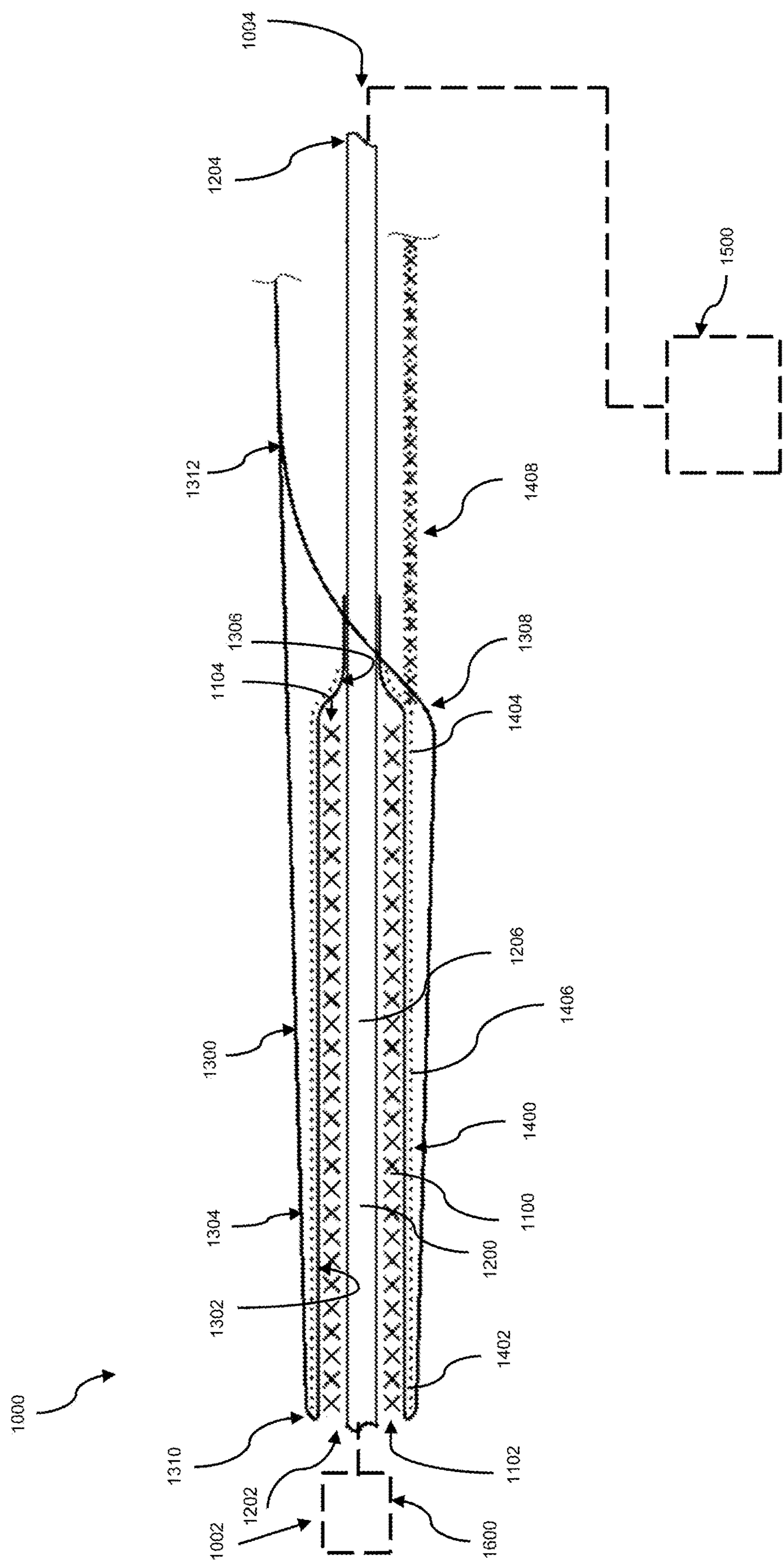
FIG. 1 is a cross-sectional illustration of a medical device delivery system, according to some embodiments.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. Additionally, it should be understood by those of skill in the art that the inventive scope of the disclosure should not be limited to the particular embodiments discussed herein.

In describing various examples, the term proximal is used to denote a position along the exemplary device proximate to or alternatively nearest to the user or operator of the device. The term distal is used to denote a position along an exemplary device furthest or further from the user or operator of the device.

Various aspects of the present disclosure are directed toward systems, apparatuses, devices, and methods for constraining, delivering, and/or deploying medical devices within the human body. Various aspects of the present disclosure also relate to systems and methods for making and using such constraining, delivering, and/or deploying apparatuses and systems.

In various embodiments, a delivery system 1000 as illustrated in FIG. 1 includes an implantable device 1100, an elongate element 1200, a cover 1300, and a constraining member 1400. The delivery system 1000 generally includes a distal end 1002 and a proximal end 1004. In various examples, the delivery system 1000 further includes a control member 1500 operably coupled to one or more of the elongate element 1200, cover 1300, and constraining member 1400. The control member 1500 may include a handle and is generally situated at or defines the proximal end 1004 of the delivery system 1000. In some examples, an olive 1600 is coupled to the elongate element 1200 such that the olive 1600 is situated at or defines the distal end 1002 of the delivery system 1000. The olive 1600 may be of any suitable size or shape as those of skill in the art will appreciate. As explained in further detail below, the control member 1500 generally provides an operator control over certain components of the delivery system 1000 illustrated and described herein, and thus facilitates a delivery of the implantable device 1100 to a treatment region within the vasculature of the body.

As mentioned above, various aspects of the disclosure are directed to constraining, delivering, and/or deploying medical devices within the vasculature of the body. In various examples, these systems, apparatuses, devices, and methods are used in conjunction with a wide variety of devices that may be temporarily or permanently deployed in a patient, including without limitation stents, stent-grafts, balloons, filters, traps, occluders, devices for delivering drugs, or other therapeutic substances or treatments, and the like. In some examples, the implantable device includes a stent portion that has one or more helical windings that are coupled together by one or more flexible strut elements or webs.

In some example push pull delivery systems, the length of the stent can impact deployment forces. In some examples including a constraining member system that unravels during deployment, the localized unraveling along length of stent helps minimize these increased forces associated with longer lengths. In some constraining member systems, longer lengths may be associated with a "bowstringing effect" as those of skill will appreciate. The sheath/constraining member system herein illustrated and described helps minimize the potential for bowstringing, and thereby helps minimize the forces associated with longer length stents. In some such examples, the tapered sheath herein illustrated and described also helps minimize frictional forces during deployment.

The terms "medical device" and "implantable device" in the present disclosure are intended to be broadly construed to encompass any device that is temporarily or permanently placed in a body including in the vasculature and other conduits within the body.

In various embodiments, the elongate element 1200 is a flexible, elongated element having proximal and distal ends and is capable of being advanced through one or more vessels to a target site or region within the vasculature. In some examples, the elongate element 1200 corresponds to a catheter shaft. Generally, however, the elongate element 1200 may be any device suitable for passage through the vasculature to a treatment region or target site. In various examples, the elongate element 1200 is advanced to a treatment region over a guidewire. In some examples, the elongate element 1200 operates as a vehicle for delivering the medical device to the treatment region. The elongate element 1200 includes a distal end 1202, a proximal end 1204, and an intermediate portion 1206 extending partially or entirely between the distal and proximal ends 1202 and 1204. In various examples, the implantable device 1100 can be mounted on or otherwise disposed about the elongate element 1200. In some such examples, the implantable device 1100 is mounted at or proximate to the distal end 1202 of the elongate element 1200 as those of skill in the art should appreciate.

In various examples, the elongate element 1200 extends from the olive 1600 or from the distal end 1002 of the delivery system 1000 to the control member 1500 or to the proximal end 1004 of the delivery system 1000. In some examples, the elongate element 1200 has a lumen extending through at least a portion of its length. In some examples, the lumen operates as a conduit such that the delivery system 1000 can be delivered over a guide wire (not shown). In some examples, the lumen additionally or alternatively operates as a working lumen that provides a passageway through which one or more medical devices (e.g., medical devices, tools, lights, and/or any other suitable therapeutic devices) may be delivered to the treatment region.

The elongate element 1200, or any portion thereof, can be comprised of any number of materials including silicone, latex, polyurethanes, polyvinyl chlorides, polyethylenes, polysiloxanes, polycarbonates, nylons, PTFE, ePTFE or other fluoropolymer, polyamides, polyimide, stainless steel, nitinol, PEEK, or any other biocompatible material, including combinations of the foregoing. Additionally, the elongate element 1200, or any portion thereof, can be hydrophilic or hydrophobic. In various examples, the elongate element 1200 can have any cross-sectional shape including, for example, a circular shape, an oval shape, a triangular shape, a square shape, a polygon shape, a uniform shape, or a non-uniform shape.

As mentioned above, in various embodiments, an olive 1600 is coupled to the elongate element 1200. In some examples, the olive 1600 is coupled to or proximate to the distal end 1202 of the elongate element 1200. The olive 1600 includes a generally tapered or frustoconically-shaped distal portion, although in some examples, the distal portion does not taper. In some examples, the olive 1600 additionally or alternatively includes a generally tapered or frustoconically-shaped proximal portion, although in some examples the proximal portion does not taper. Those of skill in the art will appreciate that the olive 1600 may be of any suitable size and shape.

Referring again to FIG. 1, the cover 1300 is disposed about an exterior periphery of the implantable device 1100. The cover 1300 generally includes a first end 1306 and a second end 1308. In various examples, the cover is adapted to surround and protect the implantable device 1100. In some examples, the cover 1300 or a portion thereof operates to constrain the implantable device 1100. The cover 1300 may be tubular in form or construction. In some examples, the cover 1300 is a sleeve that extends around or otherwise envelops a portion of or the entire implantable medical device 1100. In some examples, the cover 1300 radially constrains the implantable device 1100 (e.g., where the implantable device 1100 is configured to radially expand). In some examples, the cover 1300 additionally or alternatively operates to constrain the implantable device against longitudinal translation relative to the elongate element 1200. However, in other examples, the cover 1300 is not required to provide (or alternatively does not provide) any significant constraint to the implantable device 1100. In examples where the cover 1300 is not required to constrain the implantable device 1100, the delivery system 1000 generally includes one more constraining members, as discussed in greater detail below. In some examples, the cover 1300 is everted over itself such that an interior cover layer 1302 and an exterior cover layer 1304 are formed. In some examples, the cover 1300 is formed by bonding an interior cover layer and an exterior cover layer together at distal ends thereof to form a cover having an interior cover layer and an exterior cover layer. In various examples, each of the interior and exterior cover layers 1302 and 1304 include distal ends and proximal ends. In some examples, the proximal end of the interior cover layer 1302 is coupled to the elongate element, the distal end of the interior cover layer 1302 is coupled to (or is otherwise integral with) the distal end of the exterior cover layer 1304, and the proximal end of the exterior cover layer 1304 is everted over the interior cover layer 1302. In some such examples, one or more of the interior and exterior cover layers may be tapered as discussed herein. For example, the interior cover layer may taper between its proximal and distal ends. Likewise, in various examples, the exterior cover layer may additionally or alternatively taper between its proximal and distal ends.

In various examples, the cover 1300 is constructed from a thin and flexible material. The flexible material generally includes sufficient coverage and structural integrity to protect any bioactive coating or other surface treatment on the implantable device 1100 during manufacture, storage, delivery, and deployment. In some examples, the cover 1300 may be lubricious to help minimize damage to the medical device during manufacture, storage, delivery, and deployment. In various examples, the cover 1300 additionally or alternatively minimizes a potential for any of the components (e.g., the constraining member discussed below) that are actuated or otherwise manipulated during deployment of the medical device from snagging on or otherwise becoming entangled with the medical device.

The flexible material of the cover 1300 may be formed from a variety of different materials, including but not limited to, polytetrafluoroethylene (PTFE), expanded PTFE (ePTFE), fluorinated ethylene propylene (FEP), polyester, polyethylene, polysulfone, polyvinylidene fluorine (PVDF), polyhexafluoropropylene (PHFP), perfluoroalkoxy polymer (PFA), polyolefin, nylon, rayon, polyimide, polyamide, polypropylene, polyurethane, acrylic copolymers, and the like. In some examples, the flexible material may be in tube or sheet form, and may be formed from a continuous tube or sheet of material. For instance, the cover may be formed of one or more layers of material. These materials can also be in knitted or woven (e.g., fiber), or non-woven (e.g., felt) forms, or a composite of two or more different materials.

In some examples, layers may be laminated or otherwise mechanically coupled together, such as by way of heat treatment and/or high pressure compression and/or adhesives and/or other laminating methods known by those of skill in the art. In some examples, the cover 1300 may be formed from helically wrapping or longitudinally wrapping (e.g., cigarette wrapping) a tape about a mandrel, and/or extrusion. In some examples, the mandrel could comprise of a flat helix that has an increasing radius along the length of the mandrel. The film could be applied at angles from between (and including) forty-five (45) degrees to ninety (90) degrees for the helical wrap and a range of between (and including) zero (0) degrees to forty-five (45) degrees for the axial wrap.

In various examples, one or more of the cover 1300, the interior cover layer 1302, and the exterior cover layer 1304 is tapered or has a tapered profile along its length or a portion thereof such that a cross-section of the cover 1300 varies along a length of the cover 1300 or a portion thereof. In some examples, the taper corresponds to a diameter of the cover 1300 that varies from the first end or portion 1306 of the cover 1300 to the second end or portion 1308 of the cover 1300. In some examples, a diameter of the interior cover layer 1302 varies from the first end or portion 1306 to the fold 1310. Additionally or alternatively, in some examples, a diameter of the exterior cover layer 1304 varies from the fold 1310 to the second end or portion 1308. That is, in some examples, the cover 1300 may include a first tapering portion and a second non-tapering portion. In some examples, the diameters of the tapering portions of the cover 1300 progressively increase (or alternatively decrease) along the lengths of the tapering portions. In some examples, the progression is continuous, and may be linear or nonlinear. Additionally or alternatively, in some examples, a thickness of the cover 1300 tapers along a length of the cover 1300. That is, in some examples, one or more of an inside and an outside diameter of the cover 1300 tapers along a longitudinal length of the cover 1300. In some such examples, the inside diameter may remain constant while the outside diameter tapers along the longitudinal length of the cover 1300. Likewise, in some such examples, the outside diameter may remain constant while the inside diameter tapers along the longitudinal length of the cover 1300. The progression of the taper may be proximal or distal, and may be continuous or discontinuous, and may be linear or nonlinear, provided that the taper facilitated a reduction in interference between cover layers and/or an amount of force required to withdraw or retract the cover 1300, as those of skill will appreciate.

Figure 9:
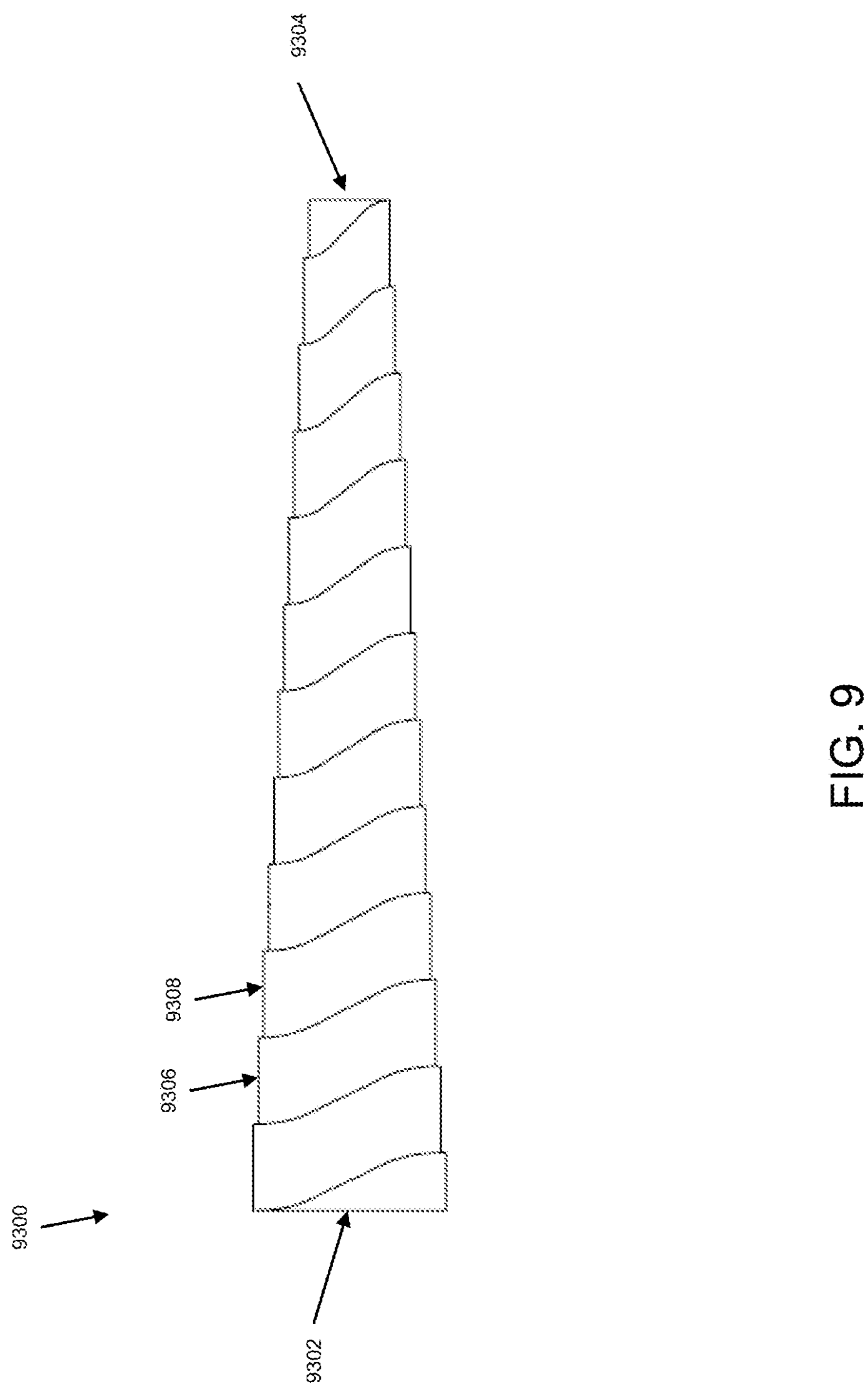
FIG. 9 is an illustration of a cover, according to some embodiments.
Figure 10:
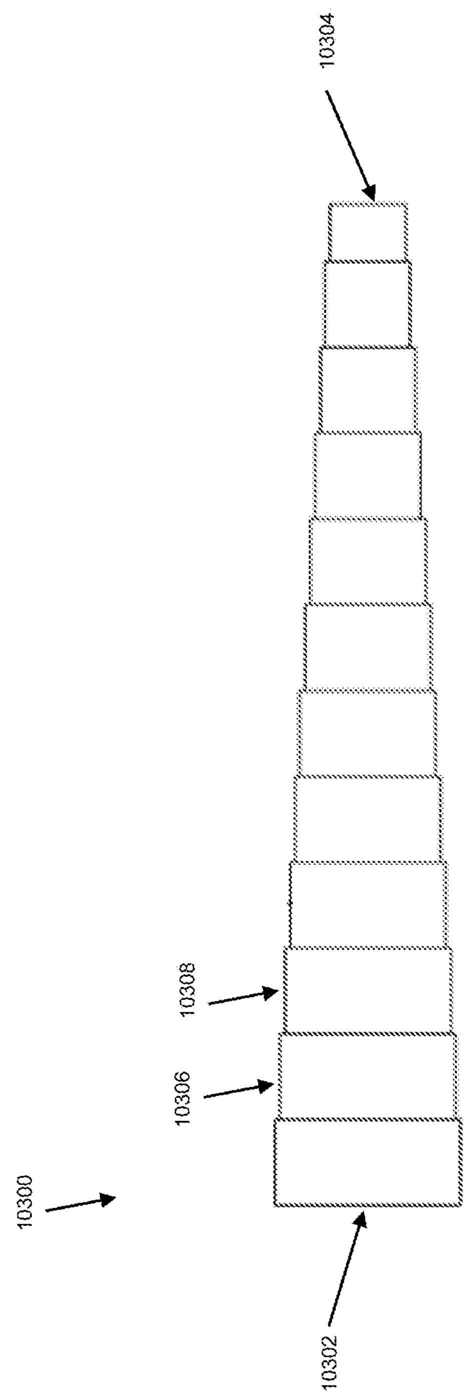
FIG. 10 is an illustration of a cover, according to some embodiments.

In some examples, however, the progression is discontinuous. For instance, in some examples, one or more of the cover 1300, the interior cover layer 1302 of the cover 1300, and the exterior cover layer 1304 of the cover 1300 includes a plurality of discrete, axially extending stepped portions (e.g., multiple discrete cylindrical sections). In some examples, the discrete stepped portions have different diameters. In some examples, each discrete stepped portion has a different diameter (e.g., multiple discrete cylindrical sections progressively increasing/decreasing in diameter along a length of the cover 1300 or a portion thereof). For example, as shown in FIG. 9, a cover 9300 includes a distal end 9302 and a proximal end 9304 and a plurality of discrete stepped portions, such as discrete portions 9306 and 9308. In some examples, the plurality of discrete stepped portions correspond to helical windings of the cover. For example, as shown in FIG. 10, a cover 10300 includes a distal end 10302 and a proximal end 10304 and a plurality of discrete helically wound stepped portions, such as discrete helically wound portions 10306 and 10308.

In some examples, one or more of the stepped portions taper along their respective lengths. In some examples, the stepped portions maintain a constant cross-section along their respective lengths (e.g., they do not taper). In various examples, a transition between each of the stepped portions is generally oriented perpendicular to a longitudinal axis of the cover. In some examples, the transitions between axial portions generally progress along the cover 1300 in a helical fashion. It should be appreciated that the cover 1300 may include 2, 3, 4, or more steps, depending on a length of the cover 1300 and a desired configuration.

In various examples, a gradient of the taper of the cover 1300 is subtle. The gradient is an average increase in diameter (e.g., interior wall or exterior wall) of the tapering portion of the cover 1300 over the length of the tapering portion of the cover 1300. For example, the diameter of the cover 1300 increases in a range of between (and including) five hundred micron (0.5 mm) and one thousand micron (1 mm) over a range of between (and including) five hundred (500) millimeters and five hundred fifty (550) millimeters. More specifically, in various examples, a diameter of the cover 1300 increases in a range of between (and including) 0.0010 to 0.0018 millimeters per millimeter of length, on average. For instance, in some examples, a diameter of the cover 1300 increases at a rate of 0.0010 millimeters per millimeter of length. In some other examples, a diameter of the cover 1300 increases at a rate of 0.0011 millimeters per millimeter of length. In some other examples, a diameter of the cover 1300 increases at a rate of 0.0012 millimeters per millimeter of length. In some other examples, a diameter of the cover 1300 increases at a rate of 0.0013 millimeters per millimeter of length. In some other examples, a diameter of the cover 1300 increases at a rate of 0.0014 millimeters per millimeter of length. In some other examples, a diameter of the cover 1300 increases at a rate of 0.0015 millimeters per millimeter of length. In some other examples, a diameter of the cover 1300 increases at a rate of 0.0016 millimeters per millimeter of length. In some other examples, a diameter of the cover 1300 increases at a rate of 0.0017 millimeters per millimeter of length. In some other examples, a diameter of the cover 1300 increases at a rate of 0.0018 millimeters per millimeter of length. In some examples, a diameter of the cover 1300 increases in a range of between (and including) 0.0013 to 0.0014 millimeters per millimeter of length. Those of skill in the art should appreciate that the above discussed cover taper ranges generally apply in embodiments including a constraining member and in embodiments without a constraining member.

As discussed in greater detail below, the tapering profile of the cover 1300 operates to reduce interference (and thus friction) between the everted and non-everted portions of the cover 1300 (or the interior and exterior cover layers) as the cover 1300 is retracted. More specifically, in some examples, the tapering profile of the cover 1300 operates to reduce interference between the interior cover layer 1302 and the exterior cover layer 1304 as the exterior cover layer 1304 is retracted relative to the interior cover layer 1302 during deployment of the implantable device 1100. Such a configuration helps to reduce an amount of force required to deploy the implantable device 1100 and also helps to minimize deployment failure and damage to the implantable device 1100 and other delivery system components that may otherwise occur as a result of higher deployment forces. Additionally or alternatively, in some examples, interference between the everted and non-everted portions of the cover 1300 are varied based on a modulus of the cover material (e.g., as the cover enlarges under radial force, the interference force increases).

In various examples, the cover 1300 can be formed by wrapping a tape around a mandrel and bonding the windings together to form the cover 1300. In various other examples, the cover 1300 can be formed through an extrusion process. In various examples, the cover 1300 can be formed by stretching a cylindrical sleeve over a mandrel into a tapered form. In various examples, one or more heat set processes may be utilized to bond windings and/or to set the form of the cover 1300, as mentioned above and as those of skill in the art will appreciate.

In various examples, the cover 1300 is configured such that it can structurally withstand the forces that may be applied to it by the various components of the delivery system 1000, including the implantable device 1100 and the constraining member 1400. Likewise, the cover 1300 is configured such that it can structurally withstand the forces exerted on it during a deployment operation where the cover 1300 splits to form a tether, as is explained in more detail below.

As mentioned above, the delivery system 1000 may further include a constraining member 1400. The constraining member 1400 may be a tubular or sleeved construct. As shown in FIG. 1, the constraining member 1400 includes a distal end 1402, a proximal end 1404, and an intermediate portion situated between the proximal and distal ends 1402 and 1404. In various examples, the constraining member 1400 operates to constrain the implantable device 1100. Specifically, the constraining member 1400 may operate to radially and/or longitudinally constrain the implantable device 1100. For example, as shown in FIG. 1, the constraining member 1400 extends over the implantable device 1100 and operates to constrain the implantable device 1100 toward a delivery configuration as discussed in greater detail below. In various examples, the constraining member 1400 is generally non-compliant (or is minimally compliant) in that it operates to resist forces exerted on it by the implantable device 1100 (e.g., radial expansion).

The constraining member 1400 may be formed from a variety of different materials, including but not limited to polytetrafluoroethylene (PTFE), expanded PTFE (ePTFE), polyester, polyethylene, polysulfone, polyvinylidene fluorine (PVDF), polyhexafluoropropylene (PHFP), perfluoroalkoxy polymer (PFA), polyolefin, nylon, rayon, polyimide, polyamide, polypropylene, polyurethane, acrylic copolymers, and the like. In some examples, the flexible material may be in tube or sheet form, and may be formed from a continuous tube or sheet of material. These materials can also be in knitted or woven (e.g., fiber), or non-woven (e.g., felt) forms, or a composite of two or more different materials.

In some examples, the constraining member 1400 includes a pleat, which operates to help facilitate radial compliance and release of the device. The pleat may be longitudinal, helical, or some combination thereof. Generally, a pleat includes any fold or multiple folds in the constraining member 1400 that reduces an effective diameter of the constraining member 1400. In some examples, a pleat includes two folds that cause the cover material to double back on itself. In some examples, a pleat includes a single fold or multiple folds along an edge of a sheet of material, which may be interlocked. Additionally or alternatively, in some examples, the pleat may also be formed through rolling or twisting a section of the material of the constraining member as those of skill in the art will appreciate. An exemplary pleated construction and method is illustrated and described in U.S. Pat. No. 8,845,712, the entire contents of which are incorporated herein by reference. In some examples the cover 1300 is additionally or alternatively pleated. In some examples, a pleat is helically oriented along at least a portion of its length. The pleat may incorporate a material or other feature that resists folding and tensile strain, such as a polyimide, to aid in creating and maintaining the pleat form and orientation. In some examples, the pleated material is everted over itself to form an interior segment and an exterior segment in the pre deployed configuration. In some such examples, one or more pleats are provided along at least a portion of the interior segment. In some examples, the application of tension to the exterior segment during deployment causes the interior segment to progressively reorient itself into the exterior segment with the pleat progressively opening proximate the transition between the interior and exterior segments. In some examples, this unpleating of the pleated material allows the unpleated exterior segment to be of sufficiently greater diameter than the pleated interior segment. Such a configuration operates to minimize frictional contact or interference between the interior segment and the exterior segment during deployment. Those of skill should appreciate that, by minimizing the frictional contact, deployment can occur with considerably less applied tension than in conventional designs.

In some examples, the constraining member 1400 may additionally or alternatively be formed from a filamentary material that is configured such that it can be unraveled or deconstructed during deployment of the implantable device 1100. For example, as discussed in greater detail below, the constraining member may be constructed of a knit filament(s) such that a break in one filament at an end of the constraining sheath facilitates progressive deconstruction of the knit-braid structure. Such a configuration provides for accurate and effective deployment of the implantable device as the deconstruction of the constraining sheath minimizes the longitudinal forces exerted on the implantable device.

In some such examples, the constraining member 1400 is woven or includes a warp knit of two or more interlocking strands of fiber or wire that together constrain the implantable device 1100. In some examples, as discussed further below, a portion of the cover 1300 is situated between the constraining member 1400 and the implantable device 1100. In some examples, the fibers or wires of the constraining member 1400 cover only a portion of the implantable device 1100. For example, the fibers or wires may be arranged such that the knit-braid of the constraining member 1400 includes one or more interstices. Additionally or alternatively, in some examples, the constraining member 1400 may be positioned such that one or more of the ends of the constraining member 1400 do not overlap or otherwise extend along one or more portions of the implantable device, as discussed further below.

In some examples, the knit-braid of the constraining member can be unraveled or deconstructed. In some examples, one or more rip cords 1408 extend from an end of the constraining member 1400. The rip cord 1408 may comprise the same material as the constraining member 1400, and thus may be continuous or integral therewith. That is, the rip cord 1408 may be a continuation of the knit-braid construction of the constraining member and may be arranged such that the rip cord is continuous therewith. Accordingly, depending on the particular knit-braid construction, the rip cord 1408 may extends from a distal end of the constraining member 1400, a proximal end of the constraining member 1400, or any portion therebetween. Those of skill will appreciate that extension of the rip cord from the distal end of the constraining member 1400 is generally associated with a distal to proximal deconstruction while extension of the rip cord from the proximal end of the constraining member 1400 is generally associated with a proximal to distal deconstruction. In some examples, the constraining member and/or rip cord are formed from polyamide, polyimide, PTFE, ePTFE, polyester or a similar material.

In some examples, the constraining member 1400 is deconstructed by imparting a break in one filament of the knit-braid at one end of the constraining member 1400. For example, the constraining member 1400 can be removed in its entirety (e.g., unraveled or deconstructed) through simple application of tension in any direction to the rip cord 1408. The rip cord 1408 may be continuous or contiguous with the constraining member 1400. That is, in some examples, the rip cord 1408 is integral with or is otherwise a continuation of the wire or fiber from which the constraining member 1400 is constructed. Additional exemplary deconstructable constraining members and their associated constructions and materials are illustrated and described in U.S. Pat. No. 6,315,792, the entire contents of which are incorporated herein by reference.

The delivery system 1000 shown in FIG. 1 is configured in a delivery configuration wherein the implantable device 1100 is situated along the elongate element 1200 near or proximate to the distal end 1202 of the elongate element 1200. As shown, the cover 1300 is disposed about the implantable device 1100. Specifically, as shown, a first end 1306 of the cover 1300 is coupled to the elongate element 1200 proximal to the proximal end 1104 of the implantable device 1100 and extends distally therefrom to a fold portion 1310. While the exemplary delivery system 1000 is shown in FIG. 1 with the cover 1300 extending to a position distal to the distal end 1102 of the implantable device 1100, those of skill in the art should appreciate that the cover 1300 may alternatively extend up to or just proximal to the distal end 1102 of the implantable device 1100. In some examples, the portion of the cover 1300 extending distal to the distal end 1102 of the implantable device 1100 includes one or more of the discrete stepped portions mentioned above. In some examples, the portion of the cover 1300 extending distal to the distal end 1102 of the implantable device 1100 includes a portion of less than all of one of the discrete stepped portions.

In some examples, as mentioned above, the cover 1300 is everted over itself and includes an interior cover layer 1302 and an exterior cover layer 1304. In some examples, as mentioned above, the cover 1300 may be formed of an interior cover layer 1302 and an exterior cover layer 1304 that are coupled at their distal ends or coupled at a different location along its length. As shown in FIG. 1, the cover 1300 includes an interior cover layer 1302 that is positioned proximate to the implantable device 1100 and an exterior cover layer 1304 that extends about at least a portion of the interior cover layer 1302. Accordingly, in various examples, the cover 1300 includes an interior cover layer 1302 that extends distally from a first end 1306 of the cover 1300 to the fold portion 1310 and an exterior cover layer 1304 that extends proximally from the fold portion 1310 toward a proximal end 1004 of the delivery system 1000. In some examples, in the delivery configuration, the fold portion 1310 is positioned distal to the first and second ends 1306 and 1308 of the cover 1300 and distal to the distal end 1102 of the implantable device 1100. Those of skill will appreciate that the fold portion 1310 may include a joint between the interior and exterior cover layers 1302 and 1304 or may define a bend where the cover 1300 is everted to form the interior and exterior cover layers 1302 and 1304. Additionally, as mentioned above, the fold portion 1310 may be positioned at or proximal to the distal end 1102 of the implantable device 1100 during delivery or while the system is in a delivery configuration.

In some examples, the cover 1300 is positioned along the implantable device 1100 such that the tapered or stepped portion of the cover 1300 is associated with the exterior cover layer 1304. That is, in some examples, the interior cover layer 1302 is non-tapered, while the exterior cover layer 1304 is tapered. In other examples, the exterior cover layer 1304 is more tapered than the interior cover layer 1302. In some examples, as discussed in greater detail below, both the interior cover layer 1302 and the exterior cover layer 1304 are tapered. In some examples, only interior layer is tapered or has discrete steps along its length. In some examples, the constraining member 1400 operates to eliminate or otherwise negate any taper that may otherwise exist along the portion of the cover 1300 about which the constraining member 1400 is disposed. In some such examples, the constraining member 1400 operates to eliminate or otherwise negate any taper of the interior cover layer 1302 about which the constraining member 1400 is disposed.

As shown in FIG. 1, the exterior cover layer 1304 tapers as it extends proximally toward the second end 1308. Specifically, as shown, the exterior cover layer 1304 tapers such that a diameter of the cover 1300 (and specifically the exterior cover layer 1304) at the fold portion 1310 is smaller than a diameter of the cover 1300 (and specifically the exterior cover layer 1304) at the second end 1308. Accordingly, a space is formed between the exterior cover layer 1304 and the portions of the delivery system 1000 about which the exterior cover layer 1304 is disposed. This configuration helps to reduce interference and friction between the exterior cover layer 1304 and the other portions of the delivery system 1000 about which it is disposed, which in turn reduces an amount of force required to deploy the implantable device 1100.

It should be appreciated that while the cover 1300 is illustrated as progressively tapering between its first and second ends 1306 and 1308, in various other examples, the cover 1300 tapers in a step-wise manner, as mentioned above. In some such examples, a cover that includes one or more stepped portions provides that, prior to retracting the cover, the interior layer and the exterior layer at the fold originate from the same step. Specifically, during manufacture of the delivery system, a cover having one or more stepped portions along at least a portion of its length is everted to create an interior cover layer and an exterior cover layer with a fold portion operating as a transition between the interior and exterior cover layers. In such examples, the cover is everted such that, in the delivery configuration, the fold portion is defined along a length of one of the step portions such that the portions of the interior and exterior cover layers proximate the fold originate from the same step portion. In configurations where the step portions maintain a generally constant cross-section along their respective lengths, such a configuration provides for a cover having generally interfering interior and exterior layers proximate the fold. Such a configuration is associated with at least an increased deployment force that helps minimize the potential for unintended predeployment of the implantable device. In some examples, such a configuration is associated with a deployment force profile that oscillates as a result of the length of interference between the interior and exterior cover layers proximate the fold, wherein for a given step portion, a maximum deployment force occurs where the fold portion bisects a given step portion (e.g., the interior and exterior cover layers proximate the fold portion have equivalent lengths and originate from the same step portion).

Additionally, as shown in FIG. 1, in various examples, the constraining member 1400 is disposed between the interior and exterior cover layers 1302 and 1304. Such a configuration helps to minimize interference between the fibers or wires forming the constraining member 1400 and features of the implantable device 1100 (e.g., anchors, barbs, apices, etc.). Additionally or alternatively, in some examples, such a configuration helps isolate or otherwise provides a barrier between the constraining member 1400 and the body or the patient's anatomy. Minimizing such interferences helps to avoid potential manufacturing difficulties (e.g., tangling, tearing, etc. of the cover, and migrations of other components during crush procedure) and/or minimize potential deployment problems (e.g., premature deployment, migration of components, unintended coating removal from the implantable device 1100, etc.).

The process for constructing the delivery system 1000 may include one or more drawing and/or crush operations. For example, the implantable device 1100 and cover 1300 may be drawing through a funnel and into the constraining member 1400. Additionally or alternatively, the cover 1300 and implantable device may be compacted by a compression apparatus, such as a radial crush device, and pulled out of the compression apparatus and into the constraining member 1400. During the crush procedure, the implantable device 1100 is transitioned from an unconstrained or expanded state to a constrained state. In the constrained state, the implantable device 1100 adopts a minimal profile and has an outside and an inside diameter that is less than an outside and an inside diameter, respectively, of the implantable device 1100 when in the unconstrained or expanded state. In some examples, in an expanded or unconstrained state or configuration, the delivery device has an unconstrained inner diameter and an unconstrained outer diameter. In some examples, in a constrained or delivery state or configuration, the delivery device has a constrained or delivery inner diameter and a constrained or delivery outer diameter. In some examples, in a deployed state or configuration, the delivery device has a deployed inner diameter and a deployed outer diameter. In some examples, the constrained delivery diameters are less than the unconstrained and deployed diameters. In some examples, the deployed diameters are less than the unconstrained diameters as those of skill in the art should appreciate.

In various examples, the constraining member 1400 operates to constrain the implantable device 1100 or otherwise help maintain a position of the implantable device 1100 along the longitudinal length of the delivery system 1000. In some examples, while the portion of the cover 1300 about which the constraining member 1400 is disposed is generally tapered, the constraining member 1400 is disposed about the cover 1300 and the implantable device 1100 such the implantable device 1100 maintains a constant delivery diameter along the length of the constraining member 1400. In some such examples, the constraining member 1400 constricts a portion of the cover 1300. Additionally or alternatively, in some examples, the cover 1300 is compliant and the radial force exerted on the cover 1300 by the implantable device 1100 causes the cover 1300 to radially expand such that an outside surface of the portion of the cover 1300 about which the constraining member 1400 is disposed contacts an inside surface of the constraining member 1400.

While the delivery system is illustrated in FIG. 1 as including a constraining member 1400 having a distal end 1402 that is generally aligned with a distal end 1102 of the implantable device 1100, in various examples, the constraining member 1400 is positioned such that the distal end 1402 extends distal to the distal end 1102 of the implantable device 1100. That is, in various examples, a portion of the constraining member 1400 may extend distal to the distal end 1102 of the implantable device 1100. In some examples, the portion of the constraining member 1400 that extends distal to the distal end 1102 of the implantable device 1100 has a diameter that is smaller than an outside diameter of the implantable device 1100 when the implantable device 1100 is in its delivery configuration (e.g., compressed and mounted on the delivery system 1000).

Additionally, it should be appreciated that the constraining member 1400 may additionally or alternatively include a portion that extends proximal to the proximal end 1104 of the implantable device 1100.

In various examples, once the cover 1300 and the implantable device 1100 are sufficiently compacted and inserted into the constraining member 1400, a length of the interior cover layer 1302 of the cover 1300 extends beyond at least the distal and proximal ends 1102 and 1104 of the compacted implantable device 1100. In various examples, this portion of the interior cover layer 1302 extending beyond the proximal end 1104 of the implantable device 1100 may be coupled to the elongate element 1200. In some examples, this portion of the interior cover layer 1302 may taper to a smaller diameter as it extends in the proximal direction, as mentioned above. That is, the cover 1300 is disposed about the implantable device 1100 such that the portion of the interior cover layer 1302 that extends proximally beyond the proximal end 1104 of the implantable device 1100 has a diameter that is the same or smaller than, on average, the portions of the interior cover layer 1302 extending along the implantable device 1100 or the exterior cover layer 1304.

In various examples, the portion of the interior cover layer 1302 extending proximally beyond the proximal end 1104 of the implantable device 1100 is generally coupled to the elongate element 1200. Those of skill in the art should appreciate that the cover 1300 may be coupled to the elongate element 1200 through any suitable measures known in the art. In various examples, the portion of the cover 1300 extending distally beyond the distal end 1102 of the implantable device 1100 is everted back over itself to form the interior and exterior cover layer 1302 and 1304, or may be coupled at a distal end thereof to a cover layer that extends thereabout. In various examples, the interior and exterior cover layers 1302 and 1304 are configured such that the constraining member 1400 is situated between the interior and exterior cover layers 1302 and 1304.

In various examples, a portion of the exterior cover layer 1304 of the cover 1300 may be split at an end of the exterior cover layer 1304 (e.g., the second end 1308 of the cover 1300) and formed into a tether 1312 (e.g., via winding, heating, or otherwise manipulating the split cover into a tethered structure) that can be withdrawn along a longitudinal length of the delivery system 1000 to withdraw the cover 1300 and deploy the implantable device 1100, as discussed in greater detail below. In other examples, the tether 1312 may alternatively be formed from a separate material that is subsequently coupled to an end of the cover 1300. In some examples, the cover 1300 is retracted without splitting or being wound into a filament. Suitable example materials for such a tether include polyamide, polyimide, PTFE, ePTFE, polyester, or any other material listed herein for use in forming the cover 1300 or the constraining member 1400. In various examples, this tether portion 1312 is coupled to the control member 1500 such that the control member 1500 can be selectively operated to withdraw the tether 1312 to cause the cover 1300 to be withdrawn from about the implantable device 1100 such that the implantable device 1100 can fully deploy.

Likewise, in various examples, the rip cord 1408 of the constraining member 1400 may be coupled to the control member 1500 such that the control member 1500 can be selectively operated to withdraw the rip cord 1408 to cause deconstruction or simultaneous deconstruction of the constraining member 1400, as explained in greater detail below. In some examples, as the rip cord 1408 is withdrawn, the rip cord 1408 is spooled or otherwise accumulated in the control member 1500.

In various examples, the delivery system 1000 is operable to cause the implantable device 1100 to be advanced through the vasculature of the patient and positioned at a treatment site within the body. Once properly positioned, the implantable device 1100 can be deployed by causing the tether portion 1312 of the cover 1300 and the rip cord 1408 of the constraining member 1400 to be actuated or withdrawn. In various examples, such actuation or withdrawal of the tether portion 1312 of the cover 1300 and the rip cord 1408 causes both a deconstruction of the constraining member 1400 and a withdrawal of the cover 1300. In such examples, deconstruction of the constraining member 1400 and a withdrawal of the cover 1300 occur simultaneously, contemporaneously, or concurrently. In some examples, deconstruction of the constraining member 1400 and a withdrawal of the cover 1300 occur simultaneously but with an initiation of the cover withdrawal lagging slightly behind an initiation of the deconstruction of the constraining member 1400, as explained in greater detail below.

Figure 2:
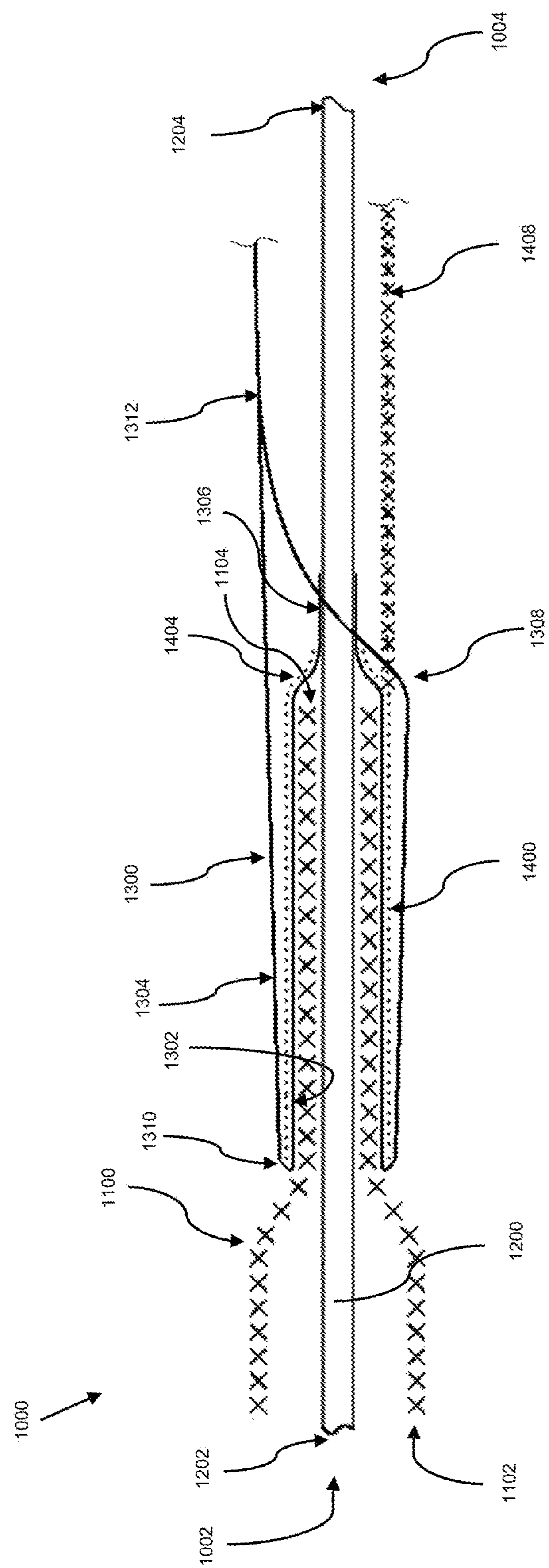
FIG. 2 is a cross-sectional illustration of the medical device delivery system of FIG. 1 in a partially deployed configuration, according to some embodiments.

In various examples, during deconstruction of the constraining member 1400, the interlocking structure of the fiber(s) or wire(s) forming the constraining member 1400 is deconstructed beginning at its distal end 1402 and advancing proximally. Specifically, the interlocking structure of the constraint 1400 progressively disengages into a long and continuous rip cord (though the rip cord is comprised of the fiber(s) or wire(s) forming the constraining member 1400). That is, instead of sliding or otherwise translating the constraining member 1400 relative to the elongate element 1200, the implantable device 1100, and the various other components of the delivery system 1000, the constraining member 1400 is deconstructed or dismantled. Thus, in various examples, the constraining member 1400 is removed without the constructed portions of the constraining member 1400 sliding relative to the implantable device 1100 or the other system components. For example, FIG. 2 shows the delivery system 1000 in a partially deployed state with a portion of the constraining member 1400 having been deconstructed. It should be appreciated that the control member 1500 and the olive 1600 have been removed for clarity purposes. Accordingly, FIG. 2 should not be viewed as excluding the control member 1500 and the olive 1600 from the delivery system 1000. As shown, the constraining member 1400 has been progressively deconstructed from its distal end such that the remaining constructed portion of the constraining member 1400 has not translated along the longitudinal axis of the delivery system 1000 (or has otherwise maintained its longitudinal position along the longitudinal axis of the delivery system 1000). As shown, a portion of the interlocking structure of the constraining member 1400 has disengaged into the rip cord 1408. Additionally, as shown the cover has been retracted to uncover at least a portion of the implantable device 1100. As mentioned above, FIG. 2 shows the delivery system 1000 in a partially deployed state wherein the implantable device 1100 is in the process of transitioning between a compressed delivery configuration and a deployed configuration. In the deployed configuration, the implantable device 1100 expands or is expanded from a constrained profile.

In various examples, as the constraining member 1400 is deconstructed, the proximal end 1404 of the constraining member 1400 generally maintains its position relative to the various other components of the delivery system 1000 as its distal end or leading end is progressively deconstructed. For example, as shown in FIG. 2, the proximal end 1404 of the constraining member 1400 has maintained its position along the longitudinal axis of the delivery system 1000. Such a configuration provides for a construct that enables deployment of the implantable device 1100 beginning at its distal end 1102 without sliding or translating the constraining member 1400 relative to the implantable device 1100 (or other components of the delivery system 1000).

In various examples, in combination with, and at times simultaneous with, the deconstruction of the constraining member 1400, the cover 1300 is withdrawn from the implantable device 1100. In various examples, as the cover 1300 is withdrawn, the fold portion 1310 rolls, advances or otherwise proximally translates along the longitudinal axis of the delivery system 1000 such that the interior cover layer 1302 progressively rolls or transitions into the exterior cover layer 1304. For example, as shown in FIG. 2, the fold portion 1310 has proximally advanced to a position along the longitudinal axis of the delivery system 1000 that is proximal to the position of the fold 1310 prior to withdrawal of the cover 1300 (see e.g., FIG. 1). As shown, this proximal progression of the cover 1300 results in a cover 1300 having an interior cover layer 1302 that rolls off of the implantable device 1100 instead of sliding along or translating relative to the implantable device 1100. Such a configuration also provides for a cover 1300 that has an interior cover layer 1302 and an exterior cover layer 1304 that are each reduced in length as the cover 1300 is withdrawn from the implantable device 1100. For example, as shown in FIG. 2, a length of the interior and exterior cover layers 1302 and 1304 are reduced relative to the length of the interior and exterior cover layers 1302 and 1304 prior to withdrawal of the cover 1300 (see e.g., FIG. 1). In some examples, while the interior cover layer 1302 rolls off of the implantable device 1100 without translating relative thereto, the exterior cover layer 1304 of the cover 1300 translates relative to both the implantable device 1100 and interior cover layer 1302 of the cover 1300.

In some examples, as the tether 1312 is withdrawn, the exterior layer 1304 additionally progressively splits and transitions into the tether 1312. In various examples, the exterior cover layer 1304 additionally progressively splits at or proximate to its second end 1308. Those of skill in the art will appreciate that any suitable mechanism may be utilized to split the exterior cover layer 1304 of the cover 1300 such that it transitions into the tether 1312. Some non-limiting suitable examples include incorporating perforations, stress risers, or other mechanical weaknesses into the material of the cover 1300, and additionally or alternatively utilizing one or more cutting edges or sharp surfaces on the delivery system 1000 to split the material of the cover 1300. As shown in FIGS. 1 and 2, the exterior cover layer 1304 splits proximate to the second end 1308 of the cover 1300 and transitions into the tether 1312. Those of skill should also appreciate that the cover 1300 need not split, as discussed herein.

In some examples, the tether 1312 is coupled to the control member 1500 such that the tether 1312 extends along the elongate element 1200 between the exterior cover layer 1304 of the cover 1300 and the control member 1500. In some examples, as the tether 1312 is withdrawn, the tether 1312 is spooled or otherwise accumulated in the control member 1500 (not shown). In some examples, the tether 1312 and/or the rip cord 1408 passes through a lumen of the elongate element 1200, as those of skill in the art will appreciate (not shown). In some examples, the lumen is in the form of a channel that may be covered or uncovered.

As mentioned above, in various examples, the deconstruction of the constraining member 1400 and a withdrawal of the cover 1300 occurs simultaneously or concurrently. For example, as shown in FIG. 2, the constraining member 1400 is being deconstructed simultaneously or concurrently with the withdrawal of the cover 1300. As shown in FIG. 2, with the constraining member 1400 partially deconstructed and the cover 1300 partially withdrawn, a portion of the implantable device 1100 is free to deploy.

In various embodiments, the delivery system 1000 can be configured such that an initiation of withdrawing the cover 1300 lags slightly relative to an initiation of deconstructing the constraining member 1400. In some examples, given the clearances and potential interferences between components of the delivery system 1000, a high degree of force may be required to initialize deployment of the various moving components of the system. Accordingly, in some examples, it is beneficial to stagger the initialization of one or more of the components. For instance, in some examples initializing deployment of the constraint 1400 prior to the cover 1300 provides that the constraint 1400 and the cover 1300 can be subsequently simultaneously actuated while maintaining a minimal deployment force.

In some examples, the constraining member 1400 is initialized prior to initializing the cover 1300. That is, in some examples, the delivery system 1000 is configured such that during deployment of the implantable device 1100, the constraining member 1400 begins unraveling prior to the cover 1300 rolling off or advancing proximally. In some examples, leading the cover removal with the deconstructions of the constraining member 1400 provides that the constraining member 1400 is not inadvertently bound up against the inside portion of the fold 1310. Put differently, by initializing the deconstruction of the constraining member 1400 before initializing the removal of the cover 1300, the delivery system 1000 can introduce an appropriate amount of lag that will avoid the fold 1310 from proximally advancing and interfering with the deconstruction of the leading end or edge of the constraining member 1400.

Figure 3:
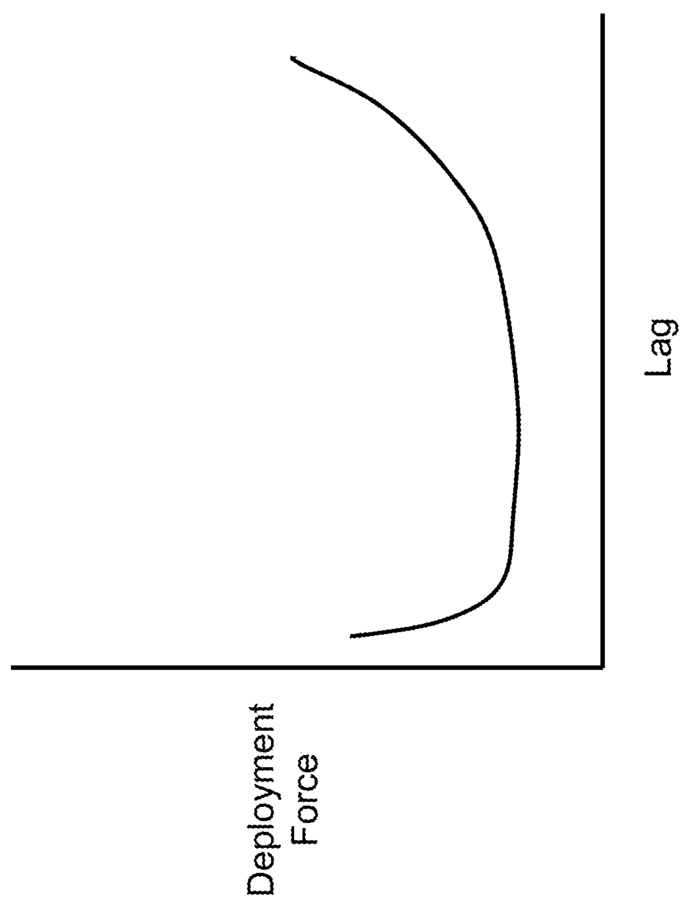
FIG. 3 is a graphical representation of a relationship between a lag and an associated deployment force, according to some embodiments.

However, introducing too much lag between the deconstruction of the constraining member 1400 and removal of the cover 1300 can cause a spike or increase in the amount of force required to continue deploying the implantable device 1100. For instance, in some examples, as the lag increases (i.e., as the distance between the leading end of the unraveling constraining member and the fold 1310 of the cover 1300 increases, a radial force exerted on the interior cover layer 1302 of the cover 1300 by the implantable device 1100 forces the interior cover layer 1302 toward the exterior cover layer 1304 of the cover 1300 (e.g., radially outward). If this radial force is strong enough and/or the area upon which this force is acting is large enough, the interior cover layer 1302 of the cover 1300 may interfere with the exterior cover layer 1304 of the cover 1300 and increase the amount of force required to continue retracting the cover 1300. An exemplary graphical illustration of the relationship between the required deployment force and the associated degree of lag is illustrated in FIG. 3. It should be appreciated that the required deployment force is depicted in units of force (e.g., pounds-force, kilogram-force, or newtons) and the lag is depicted in units of length (e.g., inches or meters), as those of skill in the art will appreciate. In some examples, a lag of less than 20 mm corresponds to a desirable deployment force such as five kilograms-force (5 kgf) or less. In some examples, the deployment force can be fifty grams-force (50 gf) or less. In some examples, a lag can exceed thirty millimeters (30 mm), forty millimeters (40 mm), fifty millimeters (50 mm), and one hundred millimeters (100 mm). In some examples, a lag can correspond to a length of the medical device (e.g., implant).

Figure 4:
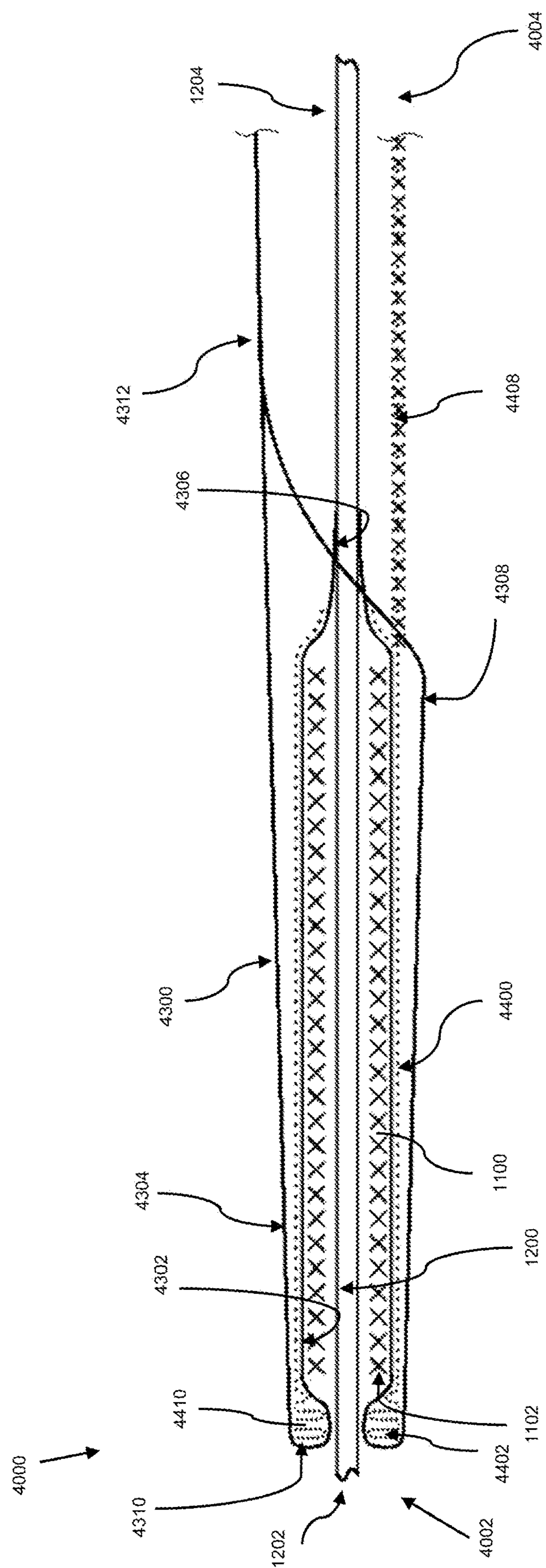
FIG. 4 is a cross-sectional illustration of a medical device delivery system, according to some embodiments.

In various examples, the lag length can is controlled by initializing the unraveling or deconstruction of the constraining member 1400 prior to retracting the cover 1300. Turning now to FIG. 4, an exemplary delivery system 4000 is illustrated and is configured to stagger the unraveling or deconstruction of the constraining member 1400 and the retraction of the cover 4300. As shown, the delivery system 4000 includes an implantable device 1100, an elongate element 1200, a cover 4300, and a constraining member 4400. In various examples, similar to the delivery system 1000, the delivery system 4000 has a distal end 4002 and a proximal end 4004 and may further include an olive and a control member operably coupled to one or more of the elongate element 1200, the cover, and constraining member 4400. Thus, while FIG. 4 does not show an olive and a control member, FIG. 4 should not be viewed as excluding a control member or an olive from the delivery system 4000. The implantable device 1100 and the elongate element 1200 are consistent with those herein illustrated and described.

The cover 4300 is consistent with the cover 1300 of the above-discussed examples with the exception that the cover 4300 operates in accordance with a constraining member 4400 that includes a scrunch, as discussed below. However, it should be appreciated that the various examples and embodiments discussed above in relation to cover 1300 (e.g., tapering) are equally applicable to cover 4300.

The constraining member 4400 is generally consistent with the constraining member 1400 described above, with some notable exceptions. Specifically, as shown in FIG. 4, a portion of the constraining member 4400 is bunched or scrunched together. Thus, in various examples, a constraining member or a portion thereof may be compacted, scrunched, bunched, accordioned, axially compressed, buckled, crumpled, or rumpled together. In some examples, the constraining member 4400 is positioned such that the scrunched portion 4410 is positioned near or proximate to the distal end 4402 of the constraining member 4400 to form a scrunch portion 4410. In some examples, the scrunch portion 4410 is formed by axially compressing (e.g., scrunching, bunching, etc.) a designated portion of the constraining member having a first axial length. In some examples, the designated portion corresponds to a length of the constraining member 4400 that extends distal to the distal end 1102 of the implantable device 1100. Once axially compressed, the designated portion of the constraining member 4400 has a second shorter axial length. In other words, in some examples, the scrunch portion 4410 is formed by axially compressing a portion of the constraining member 4400 extending distal to the distal end 1102 of the implantable device 1100 from a first axial or longitudinal length to a second shorter axial or longitudinal length.

As mentioned above, the scrunch portion 4410 of the constraining member 4400 includes a portion of the material making up the constraining member 4400 that is bunched or scrunched together. In various examples, this bunching of the material results in a scrunch portion 4410 of the constraining member 4400 that is longer in length than the longitudinal length in which it occupies. In some examples, the scrunch portion 4410 is accordion-shaped or sinusoidal as shown in FIG. 4. In various examples, like the constraining member 1400, the constraining member 4400 is deconstructable and includes a rip cord 4408 that operates in the same manner as rip cord 1408. Thus, the constraining member 4400, including the scrunch portion 4410 can be deconstructed during delivery of the implantable device 1100. In various examples, as a result of being scrunched, when unraveling or deconstructing the constraining member 4400, the scrunch portion 4410 is deconstructed along the longitudinal length of the delivery system 4000 at a slower rate than the rate at which the non-scrunched or remaining portion of the constraining member 4400 is deconstructed, as those of skill in the art will appreciate.

In various examples, the scrunch portion 4410 is situated distal to the distal end 1102 of the implantable device 1100. In some examples, the scrunch portion 4410 extends from a position distal to the distal end 1102 of the implantable device 1100 to a position adjacent to or alternatively a position proximal to the distal end 1102 of the implantable device 1100.

Additionally, as shown in FIG. 4, similar to the constraining member 1400, the constraining member 4400 is situated between layers of the cover 4300. The cover 4300 is generally consistent with the cover 1300 described above in that the cover 4300 includes an interior cover layer 4302, an exterior cover layer 4304, a first end 4306, and a second end 4308. Additionally, like the cover 1300, the cover 4300 includes a tether 4312 which is similar to tether 1312. In some examples, the cover 4300 splits as it is retracted. As shown in FIG. 4, the constraining member 4400 is situated between an interior cover layer 4302 and an exterior cover layer 4304 in a manner similar to that discussed above regarding the positioning of the constraining member 1400 between the interior and exterior cover layers 1302 and 1304 of the cover 1300. In various examples, the scrunch portion 4410 is positioned between the interior and exterior cover layers 4302 and 4304 proximate the fold 4310.

In some examples, the scrunch portion 4410 forms a bulge distal to the distal end 1102 of the implantable device 1100. In various examples, as mentioned herein, such a configuration helps minimize pre-deployment of the medical device during insertion and delivery to the target region within the body.

In various examples, during deployment of the implantable device 1100, initializations of the constraining member 4400 and the cover 4300 are staggered such that the constraining member 4400 is initialized prior to the initialization of retraction of the cover 4300. In some examples, retraction of the cover 4300 is initialized after the scrunch portion 4410 of the constraining member 4400 is entirely deconstructed. In some other examples, retraction of the cover 4300 is initialized after the scrunch portion 4410 of the constraining member 4400 is partially deconstructed.

In various examples, as mentioned above, the provision of the scrunch portion 4410 helps minimize the potential for unintended pre-deployment of the medical device during delivery to the target region within the body. For example, by initializing the deconstruction of the constraining member 4400 prior to retracting the cover 4300, the delivery system 4000 provides that an unintended actuation or activation of a component of the control member 1500 will not necessarily initiate a deployment of the implantable device 1100. Specifically, as discussed above, in some examples, the cover 4300 does not begin retracting or rolling off of the implantable device 1100 until after a portion of the constraining member 4400 is deconstructed. Thus, one more inadvertent input to a control member 1500 that would otherwise cause a retraction of the cover 4300 may only operate to initialize a deconstruction of the constraining member 4400 without also initializing a retraction of the cover 4300. In some examples, such a configuration provides that any longitudinal forces exerted on the exterior layer of the cover 4300 during delivery to the treatment site does not result in the exterior layer of the cover 4300 rolling back causing pre-deployment of the stent.

In various examples, while a scrunch portion 4410 may operate to help minimize the potential for distal migration of the implantable device 1100 along the longitudinal axis of the delivery system 4000, the delivery system 4000 may additionally or alternatively include a distal step element that operates to help minimize the potential for the cover and/or the constraining member to snag on a distal end of the medical device.

Figure 5:
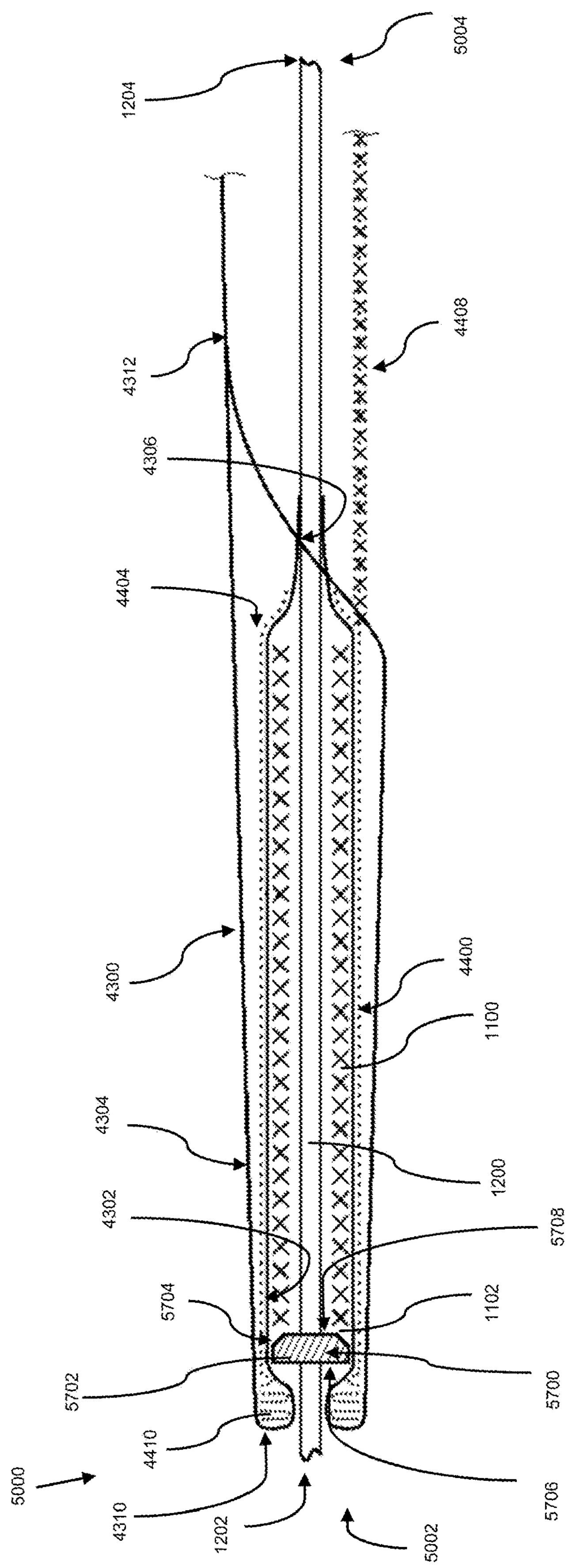
FIG. 5 is a cross-sectional illustration of a medical device delivery system, according to some embodiments.

Turning now to FIG. 5, an exemplary delivery system 5000 is illustrated as including an implantable device 1100, an elongate element 1200, a cover 4300, a constraining member 4400, and a distal step element 5700. The implantable device 1100, elongate element 1200, cover 4300, and constraining member 4400 are consistent with those herein illustrated and described. In various examples, similar to the delivery system 1000, the delivery system 5000 has a distal end 5002 and a proximal end 5004 and may further include an olive (not shown) and a control member (not shown) operably coupled to one or more of the elongate element 1200, the cover 4300, and constraining member 4400. Thus, while FIG. 5 does not show an olive and a control member, FIG. 5 should not be viewed as excluding a control member or an olive from the delivery system 5000.

In some examples, the distal step element 5700 is disposed about the elongate element 1200 and radially projects therefrom. Thus, in some examples, the distal step element 5700 is annular or ring-shaped and includes a body 5702 having an exterior surface 5704, a distal end 5706, and a proximal end 5708. In some examples, a lumen extends longitudinally through the distal step element 5700 such that the elongate element 1200 can pass therethrough.

In various examples, the distal step may be formed from pebax or any suitable suitable biocompatible material discussed herein that can be formed into the distal step construct as shown and/or described herein. In some examples, the distal step is coupled to the elongate element by way of one or more radiofrequency bonding, re-melt, or overmolding processes.

In various examples, the distal step element 5700 is positioned distal to the distal end 1102 of the implantable device 1100. In some examples, the distal step element 5700 abuts or is otherwise situated adjacent to the distal end 1102 of the implantable device 1100. In some examples, the implantable device 1100 overlays a portion of the distal step element 5700 such that a portion of less than all of the distal step element 5700 is positioned distal to the distal end 1102 of the implantable device 1100. That is, while the distal step element 5700 is illustrated with a generally flat proximal end 5708, in some examples, the proximal end 5708 may taper or step such that a proximal portion (including the proximal end 5708) can be situated proximal to the distal end 1102 of the implantable device 1100. Thus, in some examples, a portion of the distal step element 5700 is positioned beneath the implantable device 1100.

In various examples, the distal step element 5700 may additionally or alternatively operate to minimize deployment forces. For instance, in some examples, the distal step element 5700 operates as a transition. Specifically, in some examples, a distal portion of the cover 4300 and the constraining member 4400 overlay the distal step element 5700. However, because the distal step element 5700 is not configured to radially expand, the distal step element 5700 allows for a more uniform transition between the distal step outer diameter and the constrained distal apices of the implantable device 1100 as the constraining member 4400 is initially unraveled. Accordingly, as those of skill in the art should appreciate, the distal portions of the cover 4300 and constraining member 4400 that overlay the distal step element 5700 can be retracted and deconstructed, respectively, without the distal apices of the implantable device 1100 interfering with the cover 4300 and/or the constraining member 4400 upon initial deployment of the implantable device 1100.

While the distal step element 5700 is illustrated in FIG. 5 as a distinct element, in various examples, the distal step element 5700 may alternatively be configured as a feature of or a portion of an olive situated at a distal end of the delivery system 5000. That is, while some examples may include the distal step element 5700 in addition to an olive, other examples may include an olive that is configured to provide the same benefits as those discussed above with respect to the distal step element 5700. In some examples, an olive positioned at a distal end of the delivery system 5000 may include a proximal end (not shown) consistent with the proximal end 5708 of the distal step element 5700 illustrated and/or described herein. That is, in some examples, the olive may abut a distal end of an implantable device (or alternatively include a portion that is positioned proximal to and beneath the distal end 1102 of the implantable device 1100) such that, in addition to its other conventional functions, the olive additionally operates to minimize distal and/or proximal migration of the implantable device 1100 along the longitudinal axis of the delivery system 5000.

It should also be appreciated, that while the delivery system 5000 of FIG. 5 is illustrated as including a scrunch portion 4410 positioned adjacent to the distal step element 5700, in various examples, the delivery system 5000 need not include a constraining member 4400 having a scrunched or bunched portion 4410. That is, while the constraining member 4400 of some examples may include a scrunch portion 4410 that overlays and/or extends distal to a distal step element, such as distal step element 5700, in some other examples, the delivery system 5000 may include a constraining member 4400 free of a scrunch portion 4410. In some such examples, the constraining member 4400 and the cover 4300 extend distally such that they are disposed about an exterior surface of the distal step element 5700, such as exterior surface 5704. In some examples, the constraining member 4400 and the cover 4300 extend to a position distal to a distal end of the distal step element 5700, such as distal end 5706. In such examples, while the configuration of the constraining member 4400 and the cover 4300 may differ from those illustrated in FIG. 5, the distal step element itself continues to provide the same benefits illustrated and described above.

In various examples, in addition to or alternative to providing one or more mechanisms to help maintain a position (e.g., help avoid distal and/or proximal migration) of the implantable device at a position proximate to the distal end of the implantable device, in various examples, one or more mechanisms are positioned proximate to the proximal end of the implantable device to help maintain a position (e.g., help avoid distal and/or proximal migration) of the implantable device.

Figure 6:
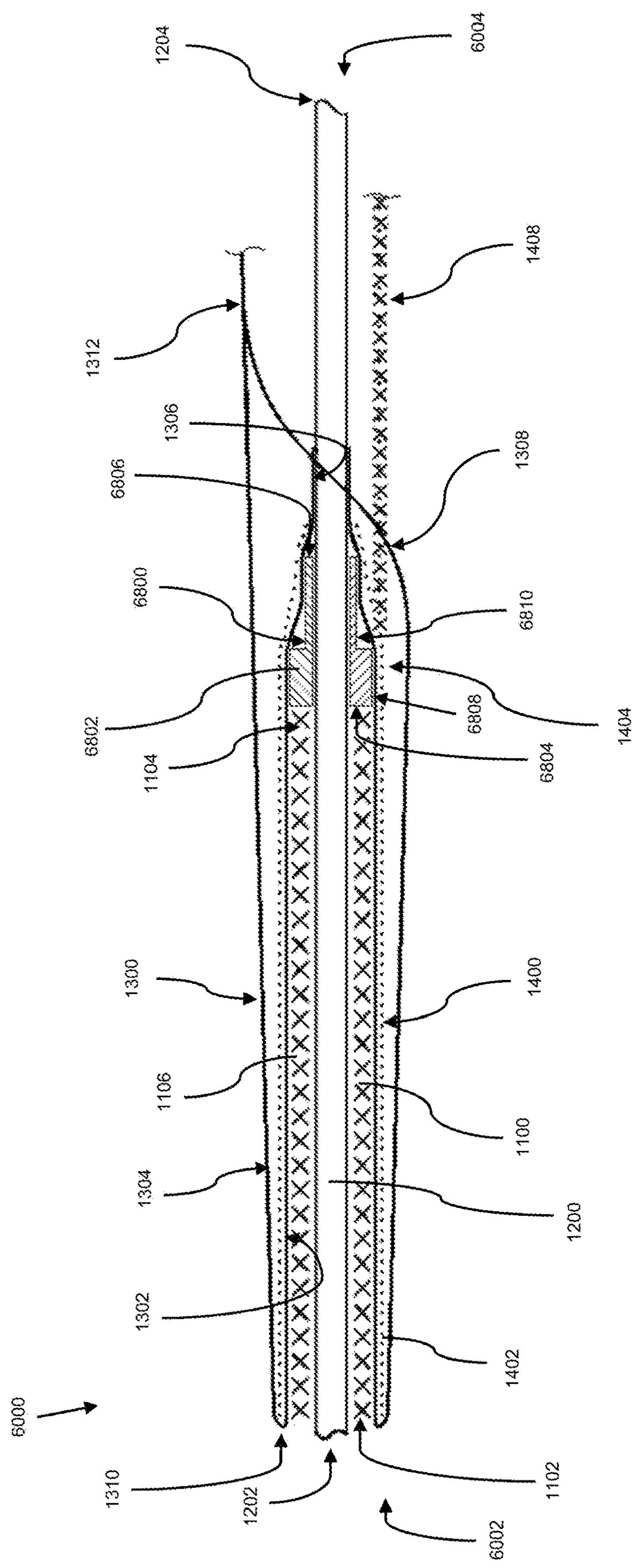
FIG. 6 is a cross-sectional illustration of a medical device delivery system, according to some embodiments.

For example, turning now to FIG. 6, an exemplary delivery system 6000 is illustrated as including an implantable device 1100, an elongate element 1200, a cover 1300, a constraining member 1400, and a proximal support element 6800. The implantable device 1100, elongate element 1200, cover 1300, and constraining member 1400 are consistent with those herein illustrated and described. In various examples, similar to the delivery system 1000, the delivery system 6000 has a distal end 6002 and a proximal end 6004 and may further include an olive (not shown) and a control member (not shown) operably coupled to one or more of the elongate element 1200, the cover 1300, and constraining member 1400. Thus, while FIG. 6 does not show an olive and a control member, FIG. 6 should not be viewed as excluding a control member or an olive from the delivery system 6000.

In some examples, the proximal support element 6800 includes a portion of the interior of the cover and the adhesive coupling the cover to the elongate element. In some other examples, the proximal support element 6800 is a separate component that is disposed about the elongate element 1200 and radially projects therefrom. In such examples, the proximal support element 6800 generally includes a body 6802 having a distal end 6804, a proximal end 6806, a first an exterior surface 6808, and a second exterior surface 6810. The first and second exterior surfaces 6808 and 6810 may be coaxial with the longitudinal axis and may extend parallel thereto, or may alternatively be angled or tapered relative thereto. In various examples, an annular surface is situated between the first and second exterior surfaces 6808 and 6810 and operates as a transition therebetween. Thus, in some examples, the first and second exterior surfaces 6808 and 6810 may have different diameters. The annular surface may be oriented perpendicular to the first and second exterior surfaces 6808 and 6810 or may alternatively be angled relative thereto. In some examples, a lumen extends longitudinally through the proximal support element 6800 such that the elongate element 1200 can pass therethrough. In various examples, the proximal support element 6800 is coupled to the elongate element 1200. The proximal support element 6800 may be coupled to the elongate element 1200 via any suitable means including but not limited to adhesives, welding, friction or interference.

In some examples, the proximal support element 6800 is formed of PATT, FEP, pebax, or any other suitable material including those described herein, and may be coupled to the elongate element in accordance with those processes discussed above regarding the distal step element.

While the proximal support element 6800 is illustrated in FIG. 6 as including the first and second exterior surfaces 6808 and 6810, it should be appreciated that the proximal support element 6800 should not be viewed as being limited to including only the first and second exterior surfaces 6808 and 6810. For instance, in some examples, the proximal support element 6800 may include a single exterior surface. Thus, in some examples, the proximal support element 6800 is annular or ring-shaped. In some examples, the proximal support element 6800 alternatively includes three (3) or more exterior surfaces, each exterior surface being stepped or offset in diameter relative to adjacently situated exterior surfaces. In some such examples, an annular surface is situated between each adjacently situated exterior surface and operates as a transition therebetween, as discussed above. In a similar manner, though not illustrated as such in FIG. 5, the distal step element 5700 may, include multiple exterior surfaces, in various examples. That is, like the proximal support element 6800, the distal step element 5700 may include two or more adjacently situated, radially offset surfaces of differing diameters.

In various examples, the proximal support element 6800 in FIG. 6 is positioned proximal to the proximal end 1104 of the implantable device 1100. In some examples, the proximal support element 6800 abuts or is otherwise situated adjacent to the proximal end 1104 of the implantable device 1100. In some examples, the implantable device 1100 overlays a portion of the proximal support element 6800 such that a portion of less than all of the proximal support element 6800 is positioned proximal to the proximal end 1104 of the implantable device 1100. That is, while the proximal support element 6800 is illustrated with a generally flat proximal end 6806 that extends between the first exterior surface 6808 and the elongate element 1200, in some examples, the proximal end 6806 may taper or include a step (e.g., an additional exterior surface radially offset from the first exterior surface 6808) such that a proximal portion (including the proximal end 6806) can be situated distal to the proximal end 1104 of the implantable device 1100. Thus, in some examples, a portion of the proximal support element 6800 is positioned beneath the implantable device 1100.

In various examples, a portion of the cover 1300 extends along or is otherwise disposed about the proximal support element 6800. For example, as shown in FIG. 6 the cover 1300 extends along the first and second exterior surfaces 6808 and 6810 of the proximal support element 6800. While the cover 1300 of FIG. 6 is illustrated as extending to a position along the elongate element 1200 proximal to the proximal end 6806 of the proximal support element 6800, it should be appreciated that the cover 1300 may terminate at or alternatively distal to the proximal end 6806 of the proximal support element 6800.

In various examples, the cover 1300 is secured or otherwise coupled to the proximal support element 6800. That is, in some examples, the proximal support element 6800 operates as an anchoring mechanism for the cover 1300. The cover 1300 may be coupled to one or more portions of the proximal support element 6800. For instance, in some examples, the cover 1300 may be secured to the proximal support element 6800 along those portions of the proximal support element 6800 about which the cover 1300 is disposed or along which it extends. Though not illustrated in FIG. 6, in some examples, the cover 1300 may additionally extend along and/or be coupled to the annular surfaces situated between the exterior surfaces of the proximal support element 6800. It should also be appreciated that the constraining member 1400 extends to a position along or alternatively proximal to the proximal support element 6800.

As mentioned above, in some examples, the constraining member 1400 is deconstructed to a position proximal to the proximal end 1104 of the implantable device 1100. In some examples, the constraining member 1400 is deconstructed to a position proximate to or otherwise adjacent with the distal end 6804 of the proximal support element 6800. In some examples, the constraining member 1400 is deconstructed to a position proximal to the distal end 6804 (and in some examples the proximal end 6806) of the proximal support element 6800.

Similarly, as mentioned above, in some examples, the cover 1300 is retracted such that the fold 1310 translates to a position proximal to the proximal end 1104 of the implantable device 1100. In some examples, the cover 1300 is retracted such that the fold 1310 translates to a position proximate to or otherwise adjacent with the distal end 6804 of the proximal support element 6800. In some examples, the cover 1300 is retracted such that the fold 1310 translates to a position proximal to the distal end 6804 (and in some examples the proximal end 6806) of the proximal support element 6800. Accordingly, in some examples, the cover 1300 is decoupled from one or more portions of the proximal support element 6800. Generally, however, the cover 1300 is retracted such that the fold 1310 maintains a position distal to the leading edge of the remaining constructed portion of the constraining member 1400.

In various examples, in addition to or alternative to providing one or more mechanisms at the proximal and distal ends of the implantable device to help maintain a position (e.g., help avoid distal and/or proximal migration) of the implantable device along the longitudinal axis of the delivery system, in various examples, one or more mechanisms are positioned between the implantable device and the elongate element to help maintain a position (e.g., help avoid distal and/or proximal migration) of the implantable device along the longitudinal axis of the delivery system.

Figure 7:
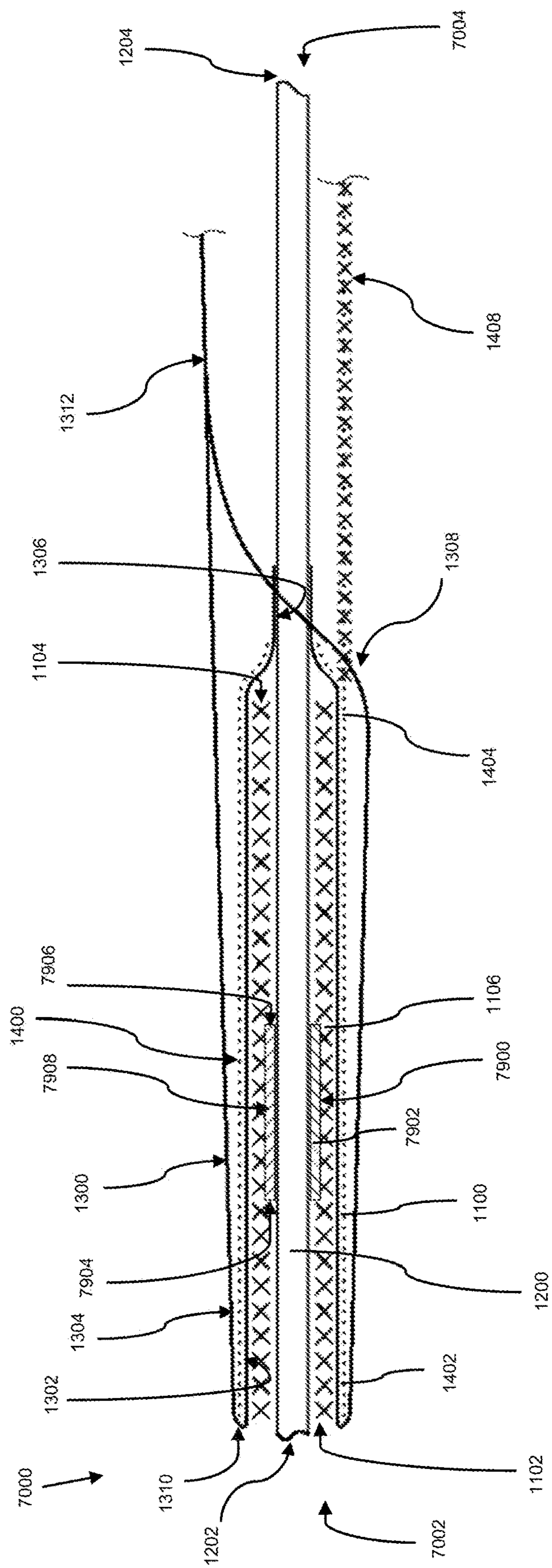
FIG. 7 is a cross-sectional illustration of a medical device delivery system, according to some embodiments.

For example, turning now to FIG. 7, an exemplary delivery system 7000 is illustrated as including an implantable device 1100, an elongate element 1200, a cover 1300, a constraining member 1400, and a intermediate support element 7900. The implantable device 1100, elongate element 1200, cover 1300, and constraining member 1400 are consistent with those herein illustrated and described. In various examples, similar to the delivery system 1000, the delivery system 7000 has a distal end 7002 and a proximal end 7004 and may further include an olive (not shown) and a control member (not shown) operably coupled to one or more of the elongate element 1200, the cover 1300, and constraining member 1400. Thus, while FIG. 7 does not show an olive and a control member, FIG. 7 should not be viewed as excluding a control member or an olive from the delivery system 7000.

In some examples, the intermediate support element 7900 is disposed about the elongate element 1200 and radially projects therefrom. The intermediate support element 7900 generally includes a body 7902 having a distal end 7904, a proximal end 7906, and an exterior surface 7908. The exterior surface 7908 is generally coaxial with the longitudinal axis and may extend parallel thereto, or may alternatively be angled or tapered relative thereto. In some examples, a lumen extends longitudinally through the intermediate support element 7900 such that the elongate element 1200 can pass therethrough. In various examples, the intermediate support element 7900 is coupled to the elongate element 1200. The intermediate support element 7900 may be coupled to the elongate element 1200 via any suitable means including but not limited to adhesives, welding, friction or interference.

In various examples, the intermediate support 7900 may be formed of soft and/or compliant biocompatible materials including pebax our any other suitable materials including those disclosed herein.

While the intermediate support element 7900 is illustrated in FIG. 7 as including a generally smooth exterior surface

7908, it should be appreciated that the exterior surface 7908 may be rough or textured. In some examples, the exterior surface 7908 may additionally or alternatively be soft or compliant to the extent that the implantable device 1100 can be partially embedded into the intermediate support element 7900.

In various examples, the intermediate support element 7900 is positioned between the proximal and distal ends 1102 and 1104 of the implantable device 1100. In some examples, a length of the intermediate support element 7900 is less than a length of the implantable device 1100. In some examples, the intermediate support element 7900 is situated adjacent to the distal end 1102 of the implantable device 1100, while in other examples the intermediate support element 7900 is situated adjacent to the proximal end 1104 of the implantable device 1100. For instance, in some examples where the implantable device is a stent-graft, the intermediate support element 7900 may be positioned such that the distal end 7904 of the intermediate support element 7900 is just proximal a distal-most row of structural supports of the stent portion of the implantable device 1100. Thus, in various examples, the implantable device 1100 overlays the body 7902 of the intermediate support element 7900. Put differently, in various examples, the intermediate support element 7900 is positioned beneath the implantable device 1100.

As mentioned above, in various examples, the intermediate support element 7900 operates to help minimize migration of the implantable device 1100 along the longitudinal axis of the delivery system 7000. In some examples, the intermediate support element 7900 operates to prevent proximal and/or distal migration of the implantable device 1100 along the longitudinal axis of the delivery system 7000.

While the various embodiments and examples illustrated above include a cover that generally tapers from a first end to a second end such that the first end is smaller in diameter than the second end, it should be understood that various other alternative configurations are envisioned and fall within the scope of the disclosure. For instance, in some examples, the cover is configured such that it has a constant cross-section, but once mounted onto the delivery system, the interior portion of the cover tapers and decreases in diameter when traversing proximally from the fold to the first end. Thus, in some examples, an exterior layer of the cover may be generally constant in cross-section while the interior layer generally varies in cross-section. Such a configuration provides that when the everted exterior layer of the cover is removed or retracted, a clearance exists between an inside of the exterior layer and the constraining member, the implantable device, and the interior layer of the cover.

In some examples, in addition to or alternative to a tapering cover, the elongate element may include one or more tapering portions such that when the everted exterior layer of the cover is removed or retracted, a clearance exists between an inside of the exterior layer, the constraining member, the implantable device, and the interior layer of the cover. Additionally or alternatively, in some examples, the constraining member is tapered such that its proximal end has a smaller outside diameter than its distal end. Such a configuration provides that a clearance exists between an inside of the exterior layer and the constraining member, the implantable device, and the interior layer of the cover.

While the various embodiments and examples are illustrated and described above with respect to FIGS. 1-7, it should be appreciated that the various components of the various delivery systems described herein may be utilized in combination with one another. For example, turning now to FIG. 8, an exemplary delivery system 8000 is illustrated as including an implantable device 1100, an elongate element 1200, a cover 8300, a constraining member 8400, a distal step element 8700, a proximal support element 8800, and an intermediate support element 8900. In various examples, the delivery system 8000 has a distal end 8002 and a proximal end 8004 and further includes a control member 1500 operably coupled to one or more components of the delivery system 8000 as discussed above. These various components of the delivery system 8000 are consistent in operation and structure to the various corresponding components of the delivery systems discussed above.

Figure 8:
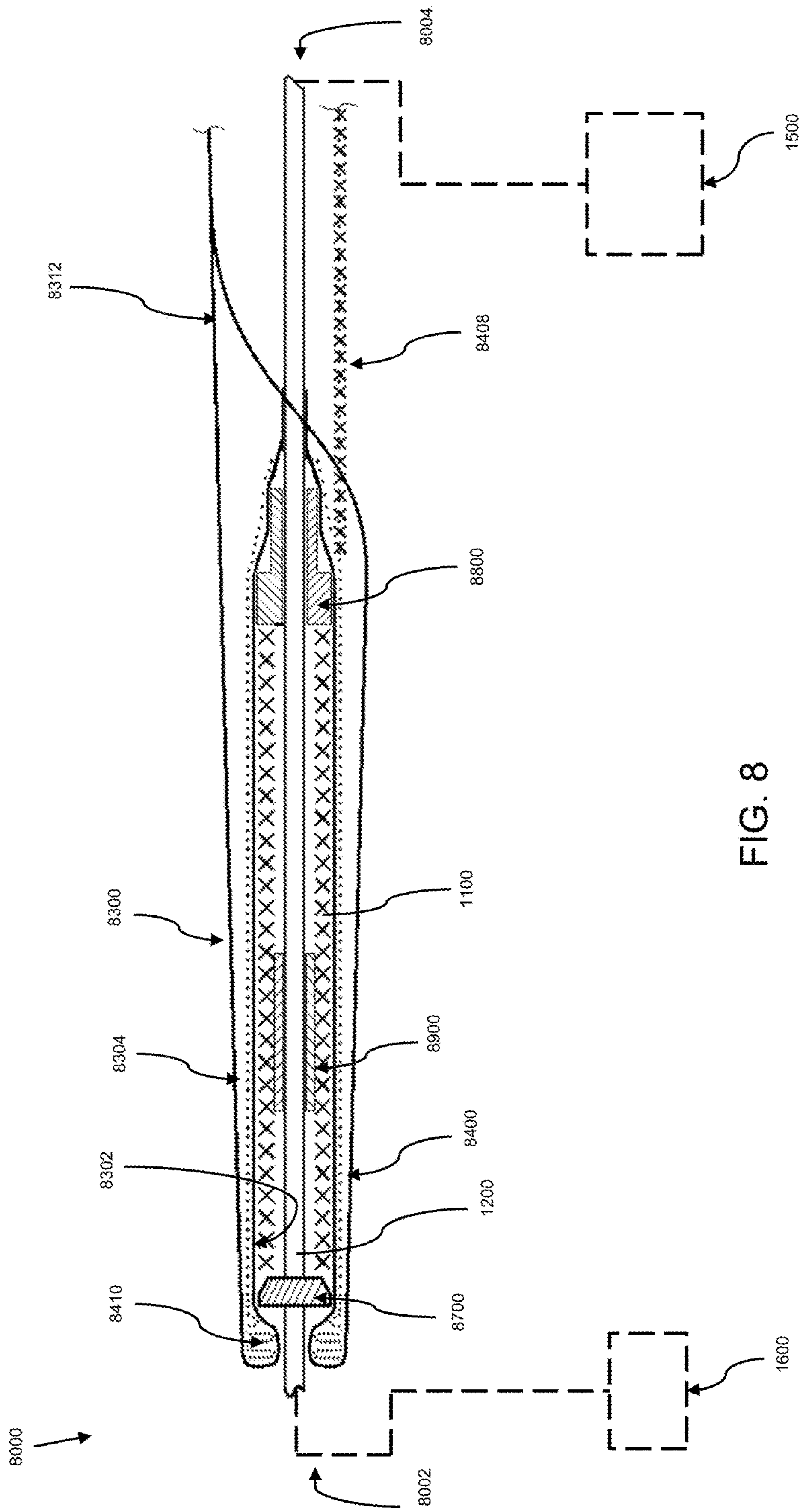
FIG. 8 is a cross-sectional illustration of a medical device delivery system, according to some embodiments.

As shown, the cover 8300 is similar to the various covers discussed above and includes at least an interior cover layer 8302, an exterior cover layer 8304, and a tether 8312. The interior cover layer 8302, an exterior cover layer 8304, and tether 8312 are similar to the various interior cover layers, exterior cover layers, and tethers discussed herein. Similarly, as shown, the constraining member 8400 is similar to the various constraining members discussed above and includes at least a rip cord 8408 and a scrunch portion 8410. The rip cord 8408 and scrunch portion 8410 are similar to the various rip cords and scrunch portions discussed herein. Likewise, the distal step element 8700, proximal support element 8800, and intermediate support element 8900 are similar to distal step element 5700, proximal support element 6800, and intermediate support element 7900, respectively, discussed above. In some examples, as shown in FIG. 8, the distal step element 8700 is positioned along the delivery system 8000 between the scrunch portion 8410 of the cover 8300 and the implantable device 1100. In some examples, the distal step element 8700 is positioned along the delivery system 8000 between the scrunch portion 8410 of the cover 8300 and the distal end of the implantable device 1100.

While certain of the examples discussed above include a constraining member that unravels, unzips, or that is otherwise deconstructed during deployment of a medical device, in various examples, the delivery system includes a constraining member that is configured to compress during deployment. In some examples, as the cover is everted or retracted, the constraining member positioned between the interior and exterior layers of the cover is compressed longitudinally along a longitudinal axis of the delivery system. In some examples, the constraining member is configured with longitudinally spaced fibers such that as the cover is everted or retracted, the fibers are forced closer to one another (e.g., the relative spacing between fibers is reduced), such that a length of the constraining member is reduced. In other words, in some examples, the delivery system includes a constraining member that is configured to have delivery length (e.g., an axial length of the constraining member prior to deployment of the medical device) and a deployment length (e.g., an axial length of the constraining member sufficient to enable full deployment of the medical device) that is shorter than the delivery length, wherein the constraining member includes a plurality of fibers spaced apart from one another along the longitudinal length of the delivery system such that the spacing between fibers is reduced to achieve the deployment length. Put differently, in some examples, a constraining member is configured to have delivery length and a deployment length that is shorter than the delivery length, an a microstructure defined by a length of fiber woven or knit to form the constraining member, wherein the constraining member is transitioned from the delivery length to the deployment length while maintaining the length of the fiber forming the constraining member. Thus, in various examples, the transition of the constraining member from the delivery length (or delivery configuration) to the deployment length (or deployment configuration) does not require or involve a deconstruction, unraveling, unknitting, or unwinding of the fibers of the constraining member.

The inventive scope of the concepts addressed in this disclosure has been described above both generically and with regard to specific examples. It will be apparent to those skilled in the art that various modifications and variations can be made in the examples without departing from the scope of the disclosure. Likewise, the various components discussed in the examples discussed herein are combinable. Thus, it is intended that the examples cover the modifications and variations of the inventive scope.

Example 1

An implantable device was obtained having an outer diameter of 8 mm and a length of 100 mm. An outer diameter of implantable device may generally range of between (and including) five (5) and twenty eight (28) millimeters or more and a length of the implantable device may generally range between (and including) forty (40) and two hundred (200) millimeters. A film sheath element was obtained, as described in U.S. Publication No. 2015-0250630 to Irwin et al., having an inner surface and an inner diameter of three (3) millimeters and a length of approximately two (2) meters.

The implantable device was pre-loaded into the cover ("film sheath element" as disclosed in U.S. Publication No. 2015-0250630 to Irwin et al.) such that the cover extended approximately thirty (30) mm beyond the implantable device proximal end and approximately one hundred eighty (180) centimeters beyond the implantable device distal end. An inner shaft made of a superelastic Nickel Titanium and having an inner diameter of 0.021 inches (e.g., within a range of between (and including) 0.020 to 0.022 inches) and an outer diameter of 0.026 inches (e.g., within a range of between (and including) 0.0024 to 0.0027 inches) was obtained. The outer diameter of the inner shaft ends were sand blasted to aid in bonding characteristics. The inner diameters of the ends were chamfered in order to help reduce friction and scraping of process mandrel and guidewire coatings.

A twenty-five (25) millimeter long (e.g., within a range of between (and including) twenty (20) to thirty-five (35) millimeters, or more) pebax jacket with a thirty-five (35) durometer hardness was melt bonded to the outside surface of the inner shaft such that the jacket had a distal end located twenty-two and a half (22.5) millimeters proximal of the distal end of the inner shaft (e.g., within a range of between (and including) two (2) to fifteen (15) millimeters proximal to the distal end of the implantable device). The jacket had an outer diameter of eight hundred ninety (890) micrometers (0.89 millimeters). An intermediate support element comprising an elastomeric material (PMVE-TFE perfluoromethylvinyl ether-tetrafluoroethylene) was wrapped at a length of approximately twenty-five (25) millimeters around the inner shaft approximately one hundred forty-one and a half (141.5) millimeters (e.g., within a range of between (and including) seventy-five (75) to two hundred fifty (250) millimeters) proximal of the distal end of the inner shaft.

The inner shaft with the anchoring mechanism material wrapped thereabout, was inserted within the sheath element inner diameter. The implantable device was contained within the film sheath element. The portion of the film sheath element inner surface extending proximal to the implantable device was bonded to the inner shaft via the anchoring mechanism such that a three (3) millimeter gap existed between the proximal end of the implantable device and the distal end of the anchoring mechanism. The inner shaft, sheath element, and implantable device were then pulled through a funnel and a constraining member as disclosed in U.S. Pat. No. 6,315,792 to Armstrong et al. The constraining member includes an approximately 0.076 inch inner diameter (e.g., within a range of between (and including) 0.065 and 0.076 inches, depending on the outer diameter of the implantable device). The diameter of the constraining member reduces as it is laid down on the device to the delivery profile, which is in the range of between (and including) five (5) to six (6) French, depending on the size of the implantable device. The constraining member was placed around the film sheath element and the implantable device, such that a proximal end of the constraining member was situated approximately thirty (30) millimeters proximal of the anchoring mechanism, and approximately thirteen (13) millimeters distal of the distal end of the implantable device.

A distal step was placed around the distal end of the inner shaft abutting the distal end of the implantable device prior to the implantable distal end of the device exiting the funnel. Subsequently, the constraining member was everted along the implantable device. During this everting action, the portion of the constraining member extending distal to the distal end of the implantable device and the distal step was longitudinally compressed such that the compressed portion would extend approximately two (2) millimeters (e.g., with a range of between (and including) one half (0.5) of a millimeter and four (4) millimeters) distal to the distal step. A stamp operation was performed on the anchoring mechanism, constraining member, and sheath element such that the outside diameter of the anchoring mechanism, constraining member, and sheath element was less than 1.19 millimeters (e.g., for a length of twenty (20) millimeters, measured from the proximal end of the anchoring mechanism). The remaining portion of the anchoring mechanism had an outer diameter of approximately 1.27 millimeters. A deployment line measuring approximately one thousand five hundred (1,500) millimeters long was then formed out of the constraining member.

The film sheath element was everted along the constraining member such that the constraining member was situated between an exterior cover layer and an inner layer of the film sheath element. A tether measuring approximately one thousand five hundred (1,500) millimeters was formed out of a portion of the exterior cover layer of the film sheath element.

The inner shaft, deployment line, and tether were fed through an outer catheter tube having a 0.056 inch inner diameter, 0.066 inch outer diameter, and 1,243 millimeter length (e.g., within a range of between (and including) 593 to 1,303 millimeters), of polycarbonate extrusion. The catheter tube included a distal end and microchannel features on its inner diameter. Specifically, the catheter tube including thirty-two (32) microchannel features (e.g., within a range of between (and including) thirty (30) to one hundred twenty (120) microchannel features) having a depth of 0.00146 inches (e.g., within a range of between (and including) 0.000185 to 0.00146 inches). The distal end of the outer catheter tube was approximately aligned with the distal end of the reduced diameter portion of the anchoring mechanism. A distal tip was bonded to the distal end of the inner shaft and a hub was bonded to the proximal end of the inner shaft. The deployment line and the tether were attached to a handle mechanism as described in U.S. Publication No.

2015-0250630 to Irwin et al. When the implantable device, with the outer sheath and constraining member mounted on an inner shaft having a jacket, was inserted through a 6 French introducer sheath, the implantable device did not predeploy.

Example 2

A mandrel was obtained having a diameter on a proximal end of approximately 4.22 millimeters and a diameter on a distal end of approximately 4.98 millimeters and with a continuous taper between the proximal end and the distal end. The mandrel had a length of approximately five hundred forty (540) millimeters. A film for a sheath element was obtained, as described in Irwin et al. The film was slit to one half (0.50) of an inch in width. The film was wrapped along the mandrel from the proximal end to the distal end of the mandrel. The film was wrapped at a helical angle of approximately eighty (80) degrees with an overlap between adjacent wraps of approximately 0.125 millimeters. Two axial ("cigarette" configuration) layers of the film were applied to the film that was helically wrapped about the mandrel. A subsequent helical wrap of film was applied at an angle of eighty (80) degrees and traversing the mandrel from the distal end to the proximal end. The mandrel with the film windings was then heated to a temperature of three hundred thirty (330) degrees Celsius for fourteen (14) minutes. The mandrel and film sheath element were then cooled at air temperature. The film sheath was removed from the mandrel and the film sheath element had a taper from the proximal end to the distal end with multiple steps along the film sheath element length. This sheath and a constraining member were assembled according to U.S. Publication No. 2015-0250630 to Irwin et al. and the resulting construction was applied over a helically wound ten (10) millimeter diameter, one hundred twenty (120) millimeter long stent made from a 0.011 inch diameter wire with twenty-five (25) apices along the stent length.

What is claimed is:

1. A medical system comprising:

an expandable endoprosthesis having a proximal end and a distal end;

an elongate member having a proximal end and a distal end, the expandable endoprosthesis being situated along the elongate member proximate the distal end of the elongate member;

a tubular cover having a first end and a second end, the cover including a first portion and a second portion, the first portion being disposed about the expandable endoprosthesis and the second portion extending over at least part of the first portion, the first portion having a diameter change such that a first end of the first portion has a smaller diameter than a second end of the first portion, wherein a space is formed between the second end of the first portion and the second portion, the space between the first portion and the second portion increasing toward the second end of the tubular cover; and a constraining member disposed about the expandable endoprosthesis such that the constraining member is situated between the first and second portions of the tubular cover, the constraining member constraining the expandable endoprosthesis in a delivery configuration.

2. The system of claim 1, wherein the second portion is everted over the first portion.

3. The system of claim 1, wherein the first portion of the tubular cover has a tapered profile.

4. The system of claim 3, wherein the tapered profile of the first portion includes a plurality of discrete steps having differing diameters.

5. The system of claim 1, wherein the tubular cover has a progressive taper from the first end of the tubular cover to the second end of the tubular cover.

6. The system of claim 1, wherein the second portion includes a diameter change.

7. The system of claim 6, wherein the tubular cover includes a plurality of stepped discrete cylindrical sections having different diameters.

8. The system of claim 7, wherein for each stepped discrete cylindrical section, the stepped discrete cylindrical section has a length and wherein a diameter is substantially constant along the length.

9. The system of claim 7, wherein one or more of the stepped discrete cylindrical sections is tapered.

10. The system of claim 1, wherein the first portion contacts the expandable endoprosthesis.

11. The system of claim 1, wherein the expandable endoprosthesis is self-expandable.

12. The system of claim 1, wherein the second portion has a length and a substantially constant diameter along the length.

13. The system of claim 1, wherein the second portion is tapered such that a proximal end of the second portion has a larger diameter than a distal end of the second portion.

14. An implantable medical device deployment system comprising:

an inner shaft having a distal end and proximal end, the medical device mounted on the inner shaft proximate the distal end of the inner shaft; and a sleeve that constrains the medical device prior to a deployment of the medical device, the sleeve adapted to unwrap from the medical device during deployment, the sleeve having a length, a proximal end, and a distal end;

wherein the sleeve includes a first section and a second section, the second section having an increased diameter relative to the first section;

wherein the second section of the sleeve is partially everted over the first section prior to the deployment of the medical device; and wherein a space is formed between the first and second sections of the sleeve, the space between the first section and the second section increasing toward the distal end of the sleeve.

15. The system of claim 14, wherein the sleeve includes a third section having an increased diameter relative to the second section.

16. The system of claim 15, wherein at least a portion of the second section is positioned distal to at least a portion of the first section and wherein the third section is positioned distal to the second section.

17. An implantable medical device deployment system comprising:

an inner shaft having a distal end and proximal end, the medical device mounted on the inner shaft near the distal end; and a knitted constraining element having a first portion and a second portion, the first portion being disposed about the medical device prior to a deployment of the medical device such that the medical device has a constrained outer diameter, the knitted constraining element being configured such that it can be deconstructed during its removal from the medical device during the deployment of the medical device, wherein the second portion of the knitted constraining element extends distal to a distal end of the medical device, the second portion of the knitted constraining element being axially compressed such that it forms a longitudinally scrunched portion, the scrunched portion being buckled.

18. The system of claim 17, further comprising a proximal support element.

19. The system of claim 17, further comprising a distal step element.

20. A medical system comprising:

an expandable endoprosthesis having a proximal end and a distal end;

an elongate member having a proximal end and a distal end, the expandable endoprosthesis being situated along the elongate member proximate the distal end of the elongate member; and a tubular cover having a first end and a second end, the tubular cover including a first portion and a second portion, the first portion being disposed about the expandable endoprosthesis and the second portion extending over at least part of the first portion, wherein at least the first portion has a plurality of discrete steps along its length, wherein a space is formed between the first and second portions of the tubular cover at the plurality of discrete steps, the space between the first portion and the second portion increasing toward the distal end of the expandable endoprosthesis.

21. The medical system of claim 20, further comprising a knitted constraining element situated between the first and second portions of the tubular cover.

* * * * *